(12) United States Patent
Multhoff

(10) Patent No.: US 7,943,740 B2
(45) Date of Patent: *May 17, 2011

(54) COMPOSITIONS AND METHODS FOR THE TREATMENT AND DIAGNOSIS OF NEOPLASTIC AND INFECTIOUS DISEASES

(75) Inventor: Gabriele Multhoff, Munich (DE)

(73) Assignee: multimmune GmbH, Munich (DE)

( * ) Notice: Subject to any disclaimer, the term of this patent is extended or adjusted under 35 U.S.C. 154(b) by 1010 days.

This patent is subject to a terminal disclaimer.

(21) Appl. No.: 10/581,918

(22) PCT Filed: Dec. 6, 2004

(86) PCT No.: PCT/EP2004/013858
§ 371 (c)(1),
(2), (4) Date: Apr. 23, 2007

(87) PCT Pub. No.: WO2005/054868
PCT Pub. Date: Jun. 16, 2005

(65) Prior Publication Data
US 2007/0280937 A1 Dec. 6, 2007

(30) Foreign Application Priority Data
Dec. 5, 2003 (EP) .................... 03028143

(51) Int. Cl.
*C07K 16/00* (2006.01)
*C12P 21/08* (2006.01)
(52) U.S. Cl. ................... 530/387.1; 530/387.3
(58) Field of Classification Search ............... 530/387.1, 530/387.3
See application file for complete search history.

(56) References Cited

U.S. PATENT DOCUMENTS

| | | | |
|---|---|---|---|
| 5,539,094 A | 7/1996 | Reed et al. | |
| 6,110,690 A * | 8/2000 | Goeddel et al. | 435/7.1 |
| 6,994,853 B1 * | 2/2006 | Lindhofer et al. | 424/136.1 |
| 2002/0155109 A1 * | 10/2002 | Lynch | 424/143.1 |
| 2005/0009033 A1 * | 1/2005 | Gray et al. | 435/6 |

FOREIGN PATENT DOCUMENTS

| | | | |
|---|---|---|---|
| WO | WO 9109967 A1 * | 7/1991 | |
| WO | 00/14106 A | 3/2000 | |
| WO | WO 0222656 A2 * | 3/2002 | |

OTHER PUBLICATIONS

Takayama et al (Cancer Res. Jul. 15, 1998;58(14):3116-31).*
Ozawa et al., Biochem. Biophy. Res. Commun., 2000, 271: 409-413.*
Kortt et al., Biomolecular Engineering, 2001, 18:95-108.*
Rudikoff et al., Proc. Natl. Acad. Sci. USA, 1982, vol. 79, 1979-1983.*
Panka et al., Proc. .Natl ..Acad. Sci. USA, 1988, vol. 85, 3080-3084.*
Amit et al., Science, 1986, 233: 747-753.*
Antoku et al., 2001, "Isolation of BCL-2 binding proteins that exhibit homology with BAG-1 and suppressor of death domains protein", Biochemical and Biophysical Research Communications, Academic Press, Sand Diego, CA, US, vol. 286(5):1003-1010.
Briknarova et al., 2002, "BAG4/SODD protein contains a short BAG domain", Journal of Biological Chemistry, vol. 277(34):31172-31178.
Eichholtz-Wirth et al., 2002, "Altered signaling of TNFalpha-TNFR1 and SODD/BAG4 is responsible for radioresistance in human HT-R15 cells", Anticancer Research, vol. 22(1A):235-240.
Takayama et al., 1999, "An evolutionarily conserved family of Hsp70/Hsc70 molecular chaperone regulators", Journal of Biological Chemistry, American Society of Biological Chemists, Baltimore, MD, US, vol. 274(2):781-786.
Takayama et al., 1998, "Expression and Location of HSP70/HSC-Binding anti-apoptotic protein BAG-1 and its variants in normal tissues and tumor cell lines", Cancer Research, American Association for Cancer Research, Baltimore MD US, vol. 58(14):3116-3131.
Townsend et al., 2002, "BAG-1 expression in human breast cancer: interrelationship between BAG-1 RNA, protein, HSC70 expression and clinico pathological data", The Journal of Pathology 197(1):51-59.

* cited by examiner

*Primary Examiner* — Hong Sang
(74) *Attorney, Agent, or Firm* — Casimir Jones, S.C.

(57) ABSTRACT

Methods and compositions for the detection, prevention and treatment of infectious diseases, primary and metastatic neoplastic diseases, including, but not limited to human sarcomas and carcinomas are provided. In particular, the detection, prevention and treatment of infectious diseases and cancer mediated and/or indicated by the presence and co-localization of a member of the anti-apoptotic Bcl-2-associated athanogene (Bag) family, especially Bag4 and membrane-bound heat shock protein (Hsp) on the cell surface of diseased tissue or cells are described.

8 Claims, 11 Drawing Sheets

COMPOSITIONS AND METHODS FOR THE TREATMENT AND DIAGNOSIS OF NEOPLASTIC AND INFECTIOUS DISEASES

This application claims the benefit of European Patent Application No. EP 03 028 143.0, filed Dec. 5, 2003.

FIELD OF THE INVENTION

The present invention relates to methods and compositions for the detection, prevention and treatment of infectious diseases, primary and metastatic neoplastic diseases, including, but not limited to human sarcomas and carcinomas. In accordance with the present invention, the practice of the prevention and treatment of infectious diseases and cancer is mediated and/or indicated by the presence and co-localization of certain tumor markers on the cell surface of diseased tissue or cells. In particular, the present invention relates to a bispecific molecule that comprises a first binding domain which binds cell surface membrane-bound heat shock protein (Hsp), preferably Hsp70, and a second binding domain which binds a member of the anti-apoptotic Bcl-2-associated athanogene (Bag) family, preferably Bag-4. Furthermore, the present invention relates to compositions comprising said bispecific molecules and their use in methods of diagnosis and treating immune response related and other diseases including tumors. The present invention further concerns the use of an antibody capable of recognizing membrane-bound Bag protein or a binding domain thereof for the detection and/or treatment of a tumor or an infectious disease.

BACKGROUND OF THE INVENTION

The era of tumor immunology began with experiments by Prehn and Main, who showed that antigens on the methylcholanthrene (MCA)-induced sarcomas were tumor specific in that transplantation assays could not detect these antigens in normal tissue of the mice (Prehn et al., J. Natl. Cancer Inst. 1 (1957), 769-778). This notion was confirmed by further experiments demonstrating that tumor specific resistance against MCA-induced tumors can be elicited in the autochthonous host, that is, the mouse in which the tumor originated (Klein et al., Cancer Res. 20 (1960), 1561-1572).

Radiation is frequently used in cancer therapy, either as a single regimen or in combination with cytostatic drugs as radiochemotherapy. However, irradiation-resistant tumor clones are limiting the therapeutic efficiency. High cytoplasmic Hsp70 levels have been found to protect tumor cells from apoptotic cell death induced by stress stimuli or exogenous compounds (Doong et al., Cancer Lett. 188 (2002, 25-32).

Heat shock proteins (Hsps) are highly conserved molecules mediating protection against lethal damage following various stress stimuli in prokaryotic and eukaryotic cells. Also under physiological conditions they support folding of non-native or misfolded proteins and prevent aggregation during proliferation and cellular differentiation (Hartl and Hayer-Hartl, Science 295 (2002), 1852-1858). The best characterized group of chaperones belong to the Hsp70 family. Like other stress proteins, Hsp70s are most efficient if they operate in concert with co-factors as cellular chaperone machineries. Together with J domain co-chaperones (i.e. Hsp40), they support protein folding and assist translocation across membranes (Pilon and Schekman, Cell 97 (1999), 679-682). ATP hydrolysis, stabilizing Hsp70-substrate complexes, is much faster in collaboration with the Hsp-interacting protein Hip (Frydman and Hohfeld, Trends Biochem. Sci. 22 (1997), 87-92). Apoptosis initiated either by exogenous factors (i.e. tumor necrosis factor α, TNFα), or spontaneous cross-linking of the death domain receptors (TNFR1, DR3) is blockable in the presence of the constitutively expressed Hsc70 and the stress-inducible Hsp70 (Jaattela, Exp. Cell Res. 248 (1999), 30-43), in concert with members of the anti-apoptotic Bcl-2-associated athanogene (Bag) family. The human members of this family are Bag-1, -2, -3, -4, -5, and 6. All of them share a highly conserved 45aa BAG domain consisting of three-helix bundles of variable length and a diverse N-terminal sequence (Takayama et al., J. Biol. Chem. 274 (1999), 781-786). Four Bag proteins (Bag-1, -3, -4, -6) have been reported to compete with Hip for binding to the ATPase domain of Hsp70s, and thus promote chaperone activity (Takayama and Reed, Nat. Cell Biol. 3 (2001), 237-241; Doong et al., Cancer Lett. 188 (2002), 25-32). It was also assumed that Bag proteins operate as cellular adaptors targeting Hsp70/Bag complexes to the cytosolic domain of the 55 kDa TNFR1, and thereby inhibit receptor aggregation and activation of the death domains via TRADD, FADD, TRAF, and RIP (Tschopp et al., Curr. Biol. 9 (1999), 381-384). Overexpression of Bag-4, also termed as the silencer of death domain (SODD) has been found to suppress TNF-induced apoptosis on the one hand (Miki and Eddy, Mol. Cell. Biol. 22 (2002), 2536-2543). On the other hand, increased Hsp70 levels confer protection against TNF-mediated lethal shock in mice (Van Molle et al., Immunity 16 (2002), 685-695). Recently, Bag proteins were discussed as important co-factors, affecting the ATPase cycle of Hsp70s (Miki and Eddy, Mol. Cell. Biol. 22 (2002), 2536-2543). The availability of hydrolyzable ATP regulates Bag binding. Apart from TNFR1, Bag proteins interact with Bcl-2, Raf-kinase, androgen-, HGF-, and PDGF receptors. Following stress, when Hsp70 levels are upregulated the Bag/receptor complexes could be replaced by Bag/Hsp70 complexes.

Although the molecular basis for the interaction between the ATPase domain of Hsp70 and the short BAG domain of Bag-4 had been elucidated in detail (Briknarova et al., Nat. Struct. Biol. 8 (2001), 349-372; Sondermann et al., Science 291 (2001), 1553-1557), knowledge on stress-induced modulations within the plasma membrane, where apoptosis might be initiated, are limited. Previously, a tumor-selective Hsp70 plasma membrane localization was demonstrated by cell surface iodination followed by SDS-PAGE and by flow cytometry of viable tumor cells, with intact plasma membrane, using an Hsp70-specific monoclonal antibody (Multhoff et al., Int. J. Cancer 61 (1995), 272-279; Ferrarini et al., Int. J. Cancer 51 (1992), 613-619). These findings are in line with recently published data (Shin et al., J. Biol. Chem. 278 (2003), 7607-7616), who uncovered an abundance of Hsp, including Hsp70, in the extracellular localized part of the plasma membrane of tumor cells by proteomic analysis of surface-bound proteins (Shin et al., J. Biol. Chem. 278 (2003), 7607-7616). Furthermore, it was found that the amount of membrane-bound Hsp70 could be modulated by treatment of tumor cells with membrane-interactive reagents (Botzler et al., Exp. Hematol. 27 (1999), 470-478) or cytostatic drugs (Gehrmann et al., J. Biol. Chem. 383 (2002), 1715-1725). Also γ-irradiation has been found to affect Hsp70 expression levels in tumor cells (Matsumoto et al., Cancer Lett. 92 (1995), 127-133; Sierra-Rivera et al., Radiat. Res. 135 (1993), 40-45; Suzuki and Watanabe, Biochem. Biophys. Res. Commun. 186 (1992), 1257-1264). Since radiation is frequently used in cancer therapy (Hennequin and Favaudon, Eur. J. Cancer 38 (2002), 223-230; Bartelink et al., Eur. J. Cancer 38 (2002), 216-222), there is medical need to understand irradiation-induced effects on the induction of apoptosis and potential mechanisms of resistance (Travis, Acta Oncol. 41 (2002), 323-333; Shinomiya, J. Cell Med. 5 (2001), 240-253).

SUMMARY OF THE INVENTION

The present invention relates to the technical field of immunology and the treatment of diseases mediated and/or indicated by the presence and co-localization of certain tumor markers on the cell surface of diseased tissue or cells. In a first aspect, the present invention relates to a bispecific molecule that comprises a first binding domain which binds cell surface membrane-bound heat shock protein (Hsp), preferably Hsp70, and a second binding domain which binds a member of the anti-apoptotic Bcl-2-associated athanogene (Bag) family, preferably Bag-4.

Furthermore, the present invention relates to a nucleic acid molecule or a composition of nucleic acid molecules encoding such bispecific molecules and cells transformed therewith, wherein said cells preferably expresses the bispecific molecule on their cell surface.

In addition, the present invention concerns the use of the mentioned bispecific molecules, nucleic acid molecules and compositions as well as cells for the preparation of a pharmaceutical composition for the targeting and/or treatment of a tumor or an infectious disease. The use of the compounds in accordance with the present invention may be accompanied by the use of further therapeutic agents such as interferons or other anti-cancer drugs.

The present invention also concerns an antibody capable of recognizing membrane-bound Bag, preferably Bag-4, or a corresponding binding molecule, a nucleic acid molecule encoding said antibody or binding molecule, or a cell expressing said antibody or binding molecule for the preparation of a pharmaceutical composition for the targeting and/or treatment of a tumor or an infectious disease.

It is also an object of the present invention to provide a method for diagnosing a radiation therapy resistant neoplastic disorder or infectious disease of a subject comprising assaying membrane-bound Bag and/or co-localization of Hsp and Bag protein on the cell surface of target cells in a sample from the subject, wherein the presence or increased amount of membrane-bound Bag and/or co-localized Hsp and Bag protein is indicative for the disorder.

It is a further object of the present invention to provide the use of NK cells or an activator of NK cells for the preparation of a pharmaceutical composition for the treatment of a tumor or infectious disease in a patient which has been positively tested according to the method of the present invention. Said NK cells may be activated prior to administration to the patient or are designed to be administered in conjunction with an activator of NK cells. Preferably, said activator comprises a peptide of Hsp70 and/or a peptide of Bag protein.

Furthermore, the present invention relates to the use of an inhibitor of the association of membrane-bound Hsp70 with a member of the anti-apoptotic Bcl-2-associated athanogene (Bag) family for the preparation of a pharmaceutical composition for the treatment of a tumor or of an infectious disease. In one embodiment said inhibitor is used as a first agent for the preparation of a pharmaceutical composition for sensitizing tumor cells or infected cells for the activity of a cytotoxic second agent.

According to another aspect, the invention relates to a method for the identification of an anti-tumor agent comprising:

(a) providing a cell expressing Hsp and Bag on its cell surface;
(b) treating said cell with at least one candidate compound; and
(c) determining whether said candidate compound interferes with the association of Hsp and Bag on the cell surface of the cell.

The present invention also concerns a kit comprising an anti-Hsp and/or anti-Bag antibody; and optionally suitable means for detection, for use in the detection of intact tumor cells or cells infected by a pathogen.

In yet another embodiment of the invention the use of an antibody specifically recognizing membrane-bound Bag protein or a binding domain thereof for the detection and/or treatment of a tumor or an infectious disease is provided. Preferably, said antibody or binding domain bind to an epitope of the C-terminal localized BAG domain. Particularly preferred are embodiments, wherein said Bag protein is Bag-4.

Histograms represent mean values of 5 independent experiments±SE; differences are indicated as p values.

Figure 5:
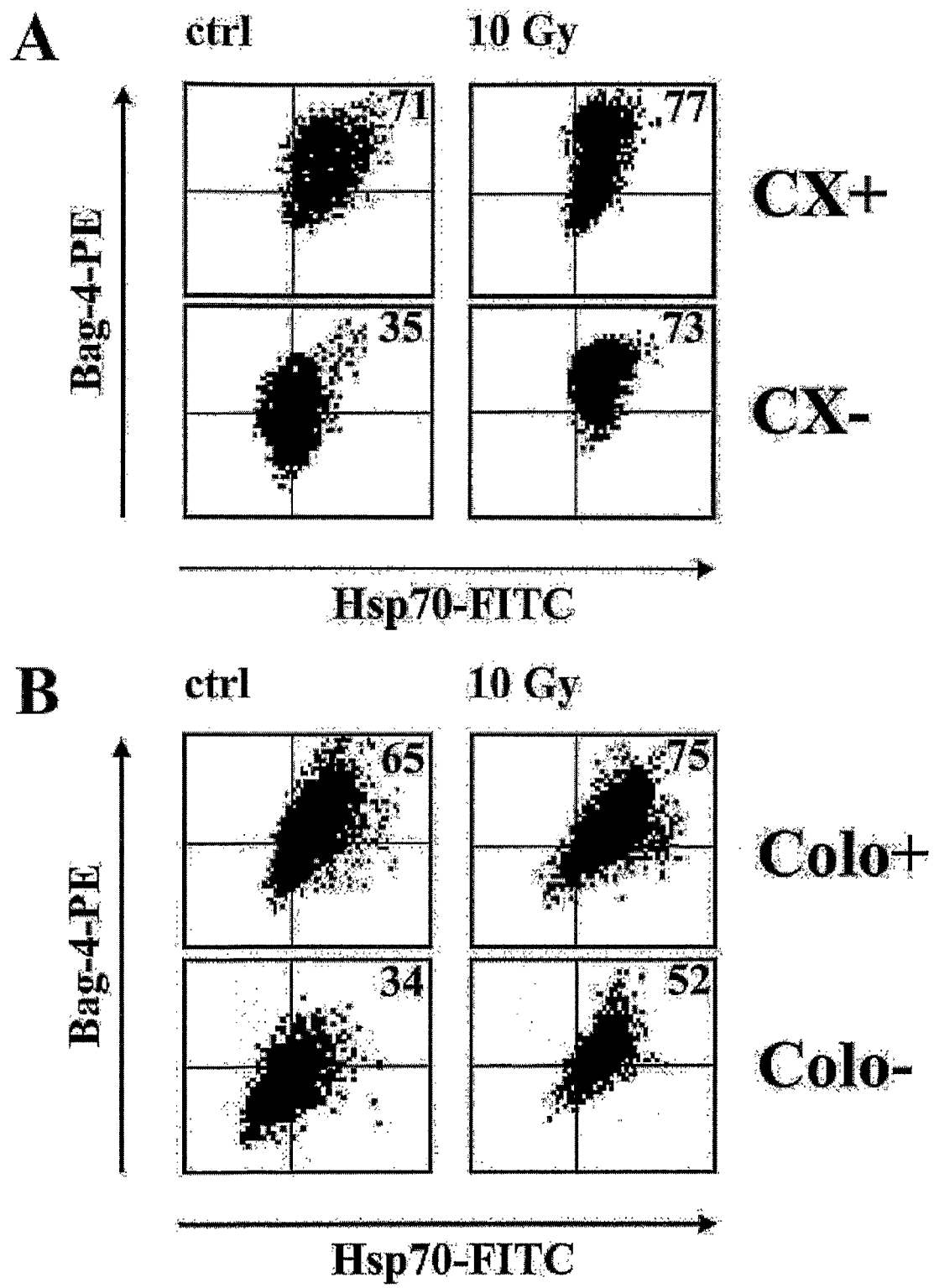
Figure 5:
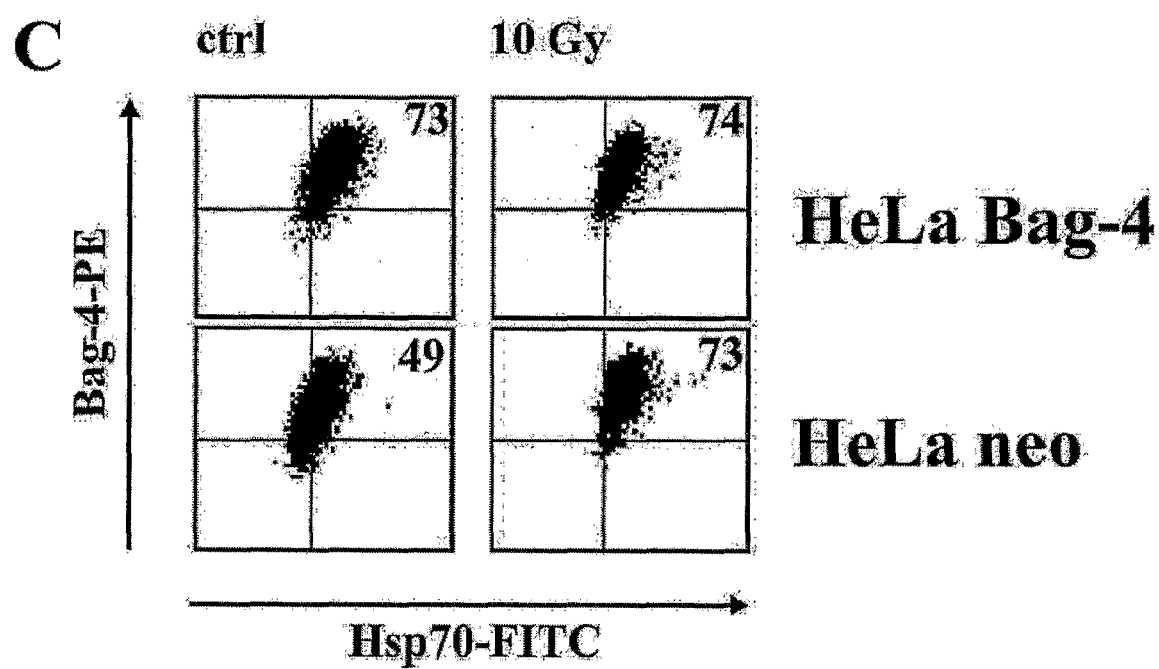

FIG. 5: Following γ-irradiation the Hsp70/Bag-4 double-positive cell population is upregulated in Hsp70/Bag-4-low expressing carcinoma sublines. Carcinoma sublines CX+/CX− (A), Colo+/Colo− (B), HeLa Bag-4/HeLa neo (C) were double-stained with Hsp70 FITC and Bag-4 PE and analysed by multiparameter flow cytometry. Values represent percentage of double-positive stained cells corrected for the non-specific staining using isotype-matched control antibodies. Only 7-AAD-negative, viable cells were gated. Dot blots illustrate one representative staining pattern of three identical experiments; mean values of Hsp70/Bag-4 positively stained cells are indicated as percentages in the upper right corner of each graph.

Figure 6:
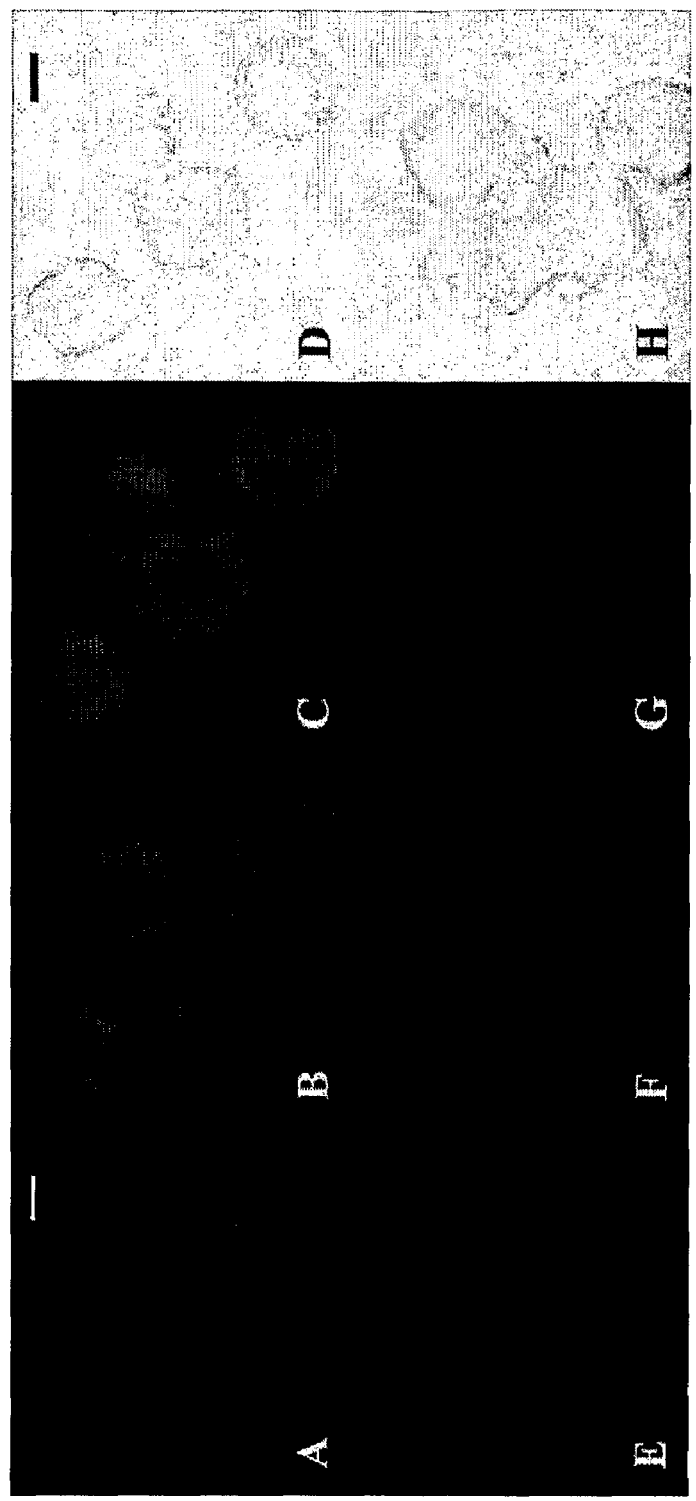
Figure 6:
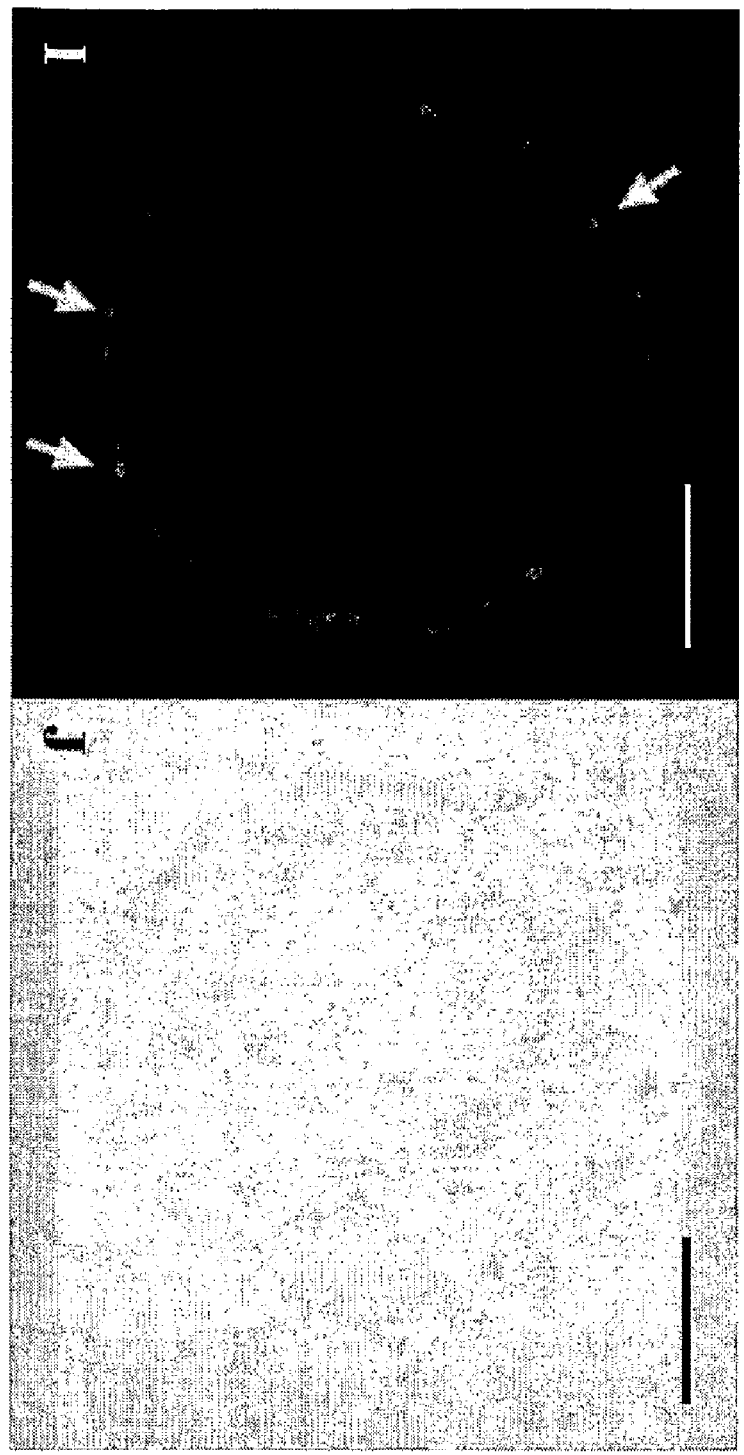

FIG. 6: Hsp70/Bag-4 are co-localized on the cell surface of carcinoma cells. CX+ cells were co-stained at 4° C. with the Bag-4 PE- (A) and the Hsp70 FITC (B)-conjugated anti-body or with isotype-matched control antibodies (E, F, G). Cells were mounted on slides and analysed on a fluorescence microscope. Bag-4 positively stained cells are visible in red, Hsp70 positively stained cells in green; co-localization, as an overlay of the red and green fluorescence (C) is visible in yellow. Graph I represents a higher magnification of a double-positive tumor cell. Corresponding light microscopical views are shown in graphs D, H and J. Experiments showing similar results were repeated with identical results for Colo+ cells. Scale bar, 10 μm.

Figure 7:
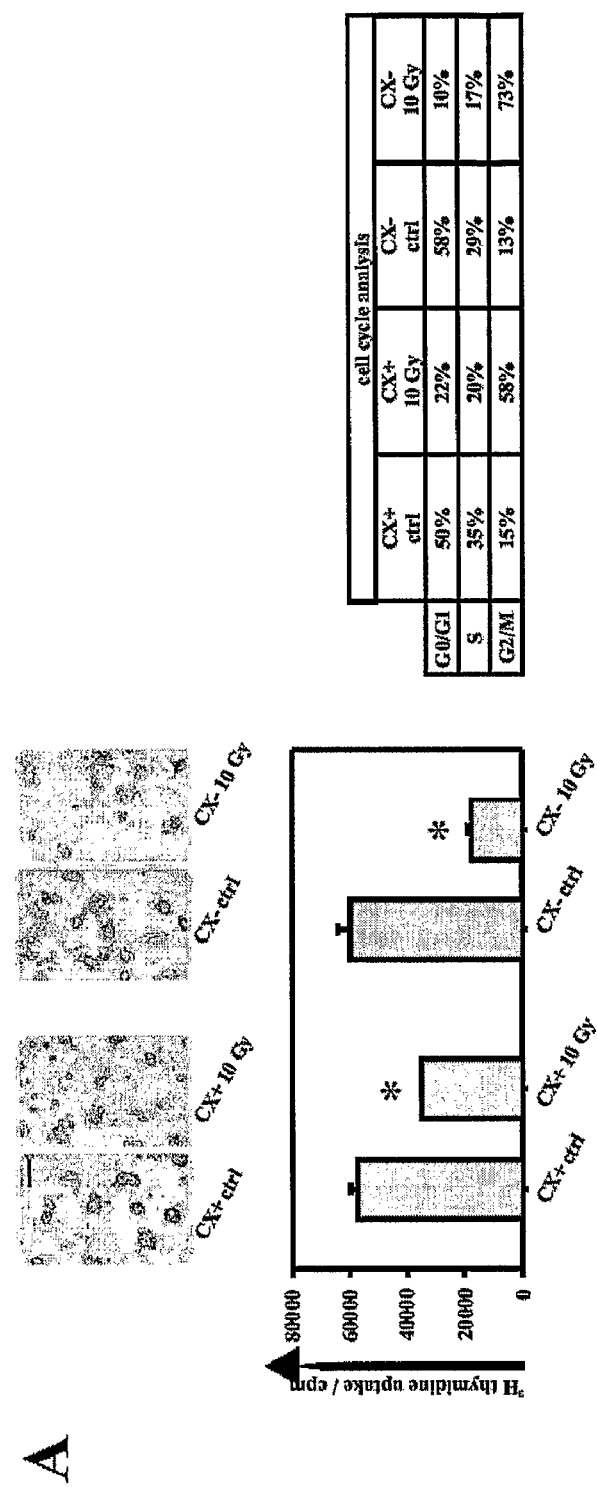
Figure 7:
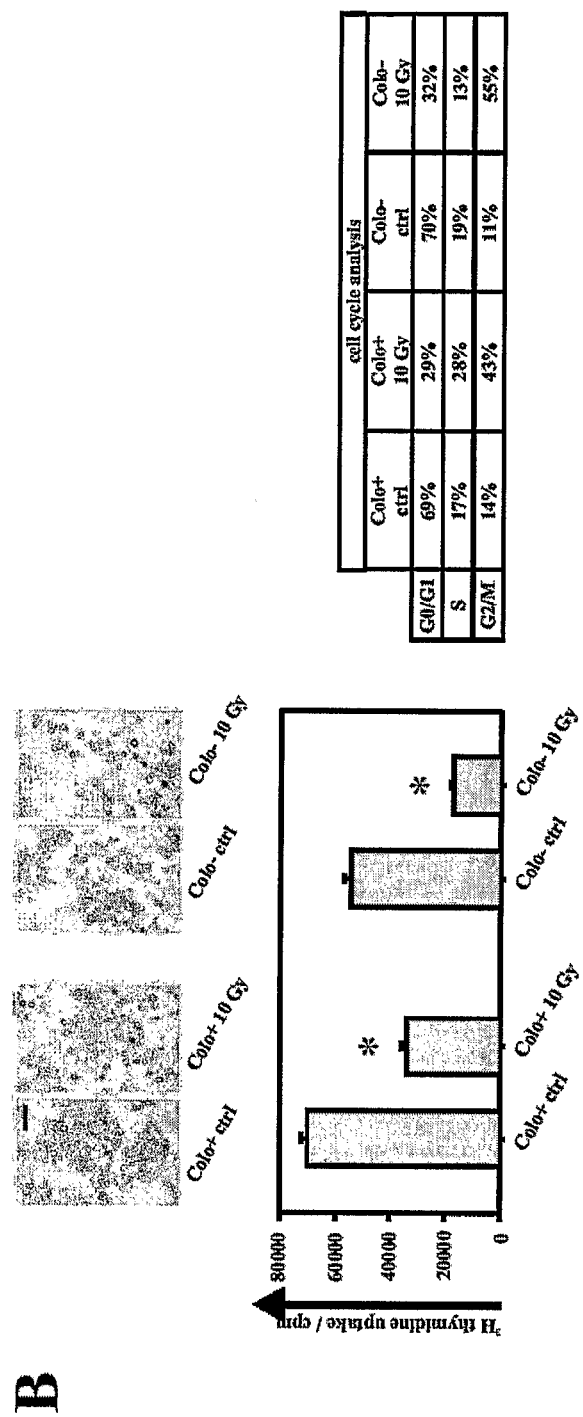
Figure 7:
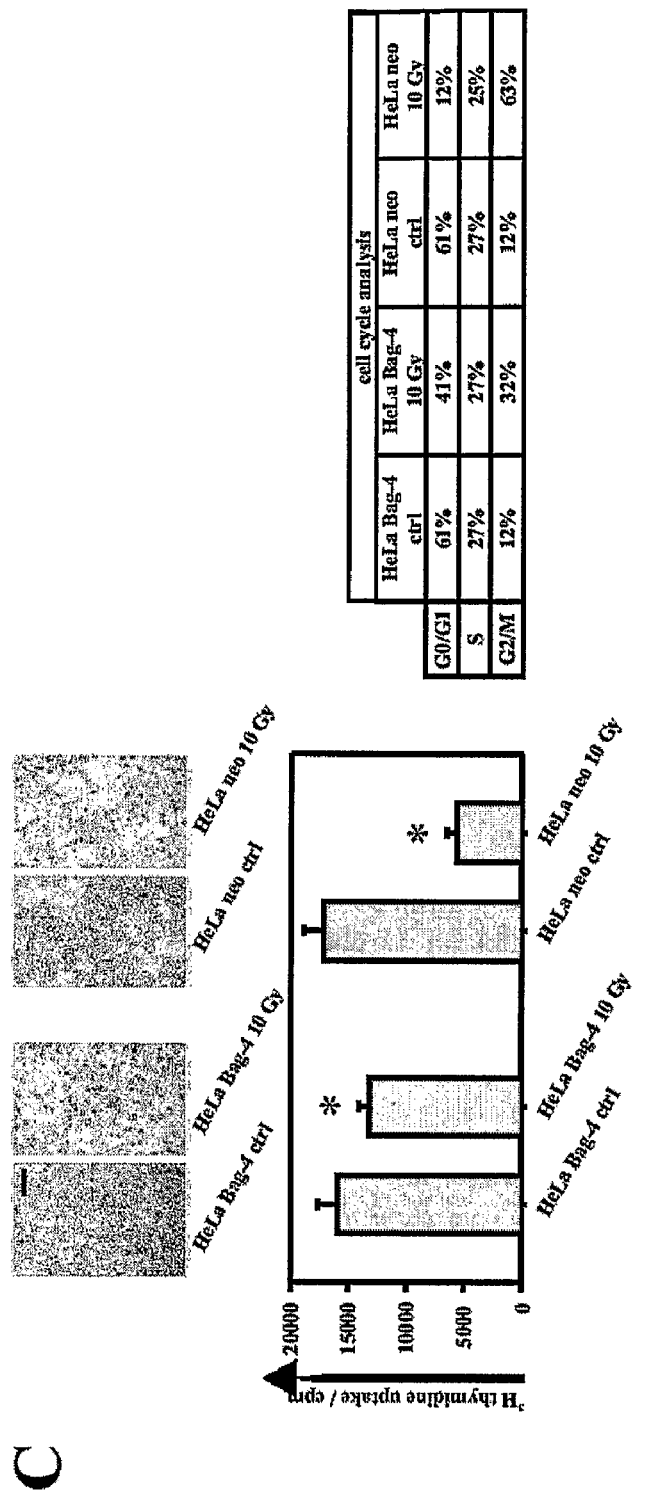

FIG. 7: Hsp70/Bag-4-low expressing carcinoma sublines are more sensitive to γ-irradiation-induced effects as compared to their high expressing counterparts. Light microscopical analysis, $^3$H thymidine uptake and cell cycle analysis of either untreated (ctrl) or irradiated (10 Gy) CX+/CX− (A), Colo+/Colo− (B), and HeLa Bag-4/HeLa neo (C) cells are illustrated. Inhibition of cell growth and G2/M arrest was significantly (*, p<0.05) more pronounced in Hsp70/Bag-4-low expressing carcinoma cells as compared to their Hsp70-Bag-4-high expressing counterparts. Scale bar, 200 μm.

DETAILED DESCRIPTION OF THE INVENTION

The present invention relates to methods and compositions for the diagnosis, prevention and treatment of primary and metastatic neoplastic diseases and infectious diseases and for eliciting an immune response in a human individual. In particular, according to one aspect of the invention, a bispecific molecule that comprises a first binding domain which binds cell surface membrane-bound heat shock protein (Hsp) and a second binding domain which binds a member of the anti-apoptotic Bcl-2-associated athanogene (Bag) family is described, wherein as explained below said Bag protein is likewise exposed on the cell membrane.

The present invention is based on the observation of the dual function of heat shock protein 70 (Hsp70)/Bag-4 membrane expression on carcinoma cells, which confer resistance to γ-irradiation and present a target for natural killer (NK) cells. In accordance with the present invention the impact of irradiation-induced effects in three independent carcinoma cell systems that differ with respect to their capacity to express Hsp70 on the cell surface was investigated. Concomitantly, the expression of Bag-4, as an Hsp70-interacting, anti-apoptotic molecule was investigated. Colon (CX+/CX−) and pancreas (Colo+/Colo−) carcinoma sublines with stable Hsp70-high and -low membrane expression were established by Hsp70 antibody-based cell sorting. Although different in their cell surface pattern, the cytoplasmic Hsp70 levels were identical in all tumor sublines, even following sublethal γ-irradiation. Interestingly, membrane-bound Hsp70 was associated with cell surface localization of the silencer of death domain Bag-4, known to interact with the ATPase domain of Hsp70. Co-localization of Hsp70/Bag-4 on the cell surface was demonstrated by dual staining flow cytometry and immunocytochemistry. After sublethal γ-irradiation, the amount of membrane-positive cells and the mean fluorescence intensity of Hsp70/Bag-4 were selectively enhanced in CX− and Colo−carcinoma sublines with initial low cell surface expression levels.

In addition to radiation, the effects of Bag-4 overexpression on Hsp70 expression were analysed. Stably Bag-4-transfected HeLa cervix carcinoma cells, displayed a 4-fold increase in cytosolic Bag-4 levels, as compared to untransfected or neo-vector transfected HeLa cells. Concomitantly, membrane-expression of Bag-4 and Hsp70 was up-regulated. In response to γ-irradiation untransfected and neo-transfected HeLa cells reacted similarly to Hsp70/Bag-4-low expressing carcinoma sublines CX− and Colo−, whereas Bag-4-transfected HeLa cells were comparable to Hsp70/Bag-4-high expressing sublines CX+ and Colo+. With respect to these findings a co-regulated Hsp70/Bag-4 cell surface expression is assumed.

Functionally, membrane-bound Hsp70 in association with Bag-4 confers protection against γ-irradiation-induced effects, including G2/M arrest and growth inhibition. In contrast, irradiation-resistant, Hsp70/Bag-4-high expressing carcinoma sublines provide ideal targets for the cytolytic attack mediated by natural killer (NK) cells.

Without intending to be bound by theory it is believed that since Hsp and Bag proteins play a major role in immune responses as well as in the apoptotic pathway and have been found by the inventors to interact with each other, and being expressed on a specific subset of cells, it is reasonable to assume that agents modulating their interaction and/or activity will have beneficial, additive and preferably synergistic effects on the treatment of diseases and conditions, wherein either or both proteins are involved in. Furthermore, such agents are expected to be useful in diagnosis, where the presence or absence of either or both proteins is associated with said disease or condition. Accordingly, the present invention provides novel bispecific molecules which have binding specificity for Hsp and Bag. Certain bispecific molecules of the present invention are used for binding to antigen or to block interaction of a protein and its ligand; their use to promote interactions between immune cells and target cells however is preferred. Finally, antigen-binding molecules of the invention are used to localize immune cells, tumor cells, infected cells, anti-tumor agents, target moieties, reporter molecules or detectable signal producing agents to an antigen of interest.

In accordance with the above and as illustrated in the examples, the bispecific molecules of the present invention as well as the later described anti-Bag antibody are preferably capable of specifically binding their target antigen on a subset of viable cells, i.e. preferably tumor cells. For tumor diagnostics, for example, the bispecific molecules and antibodies, respectively, are thus particularly advantageous since their use make further preparation of the cell sample superfluous and in addition allow histochemical analyses.

In a particularly preferred embodiment of the bispecific molecule of the present invention said Hsp is Hsp70 and said Bag is Bag-4. The nucleic and amino acid sequences of Bag including Bag-4 are described in the prior art; see, e.g., WO00/14106 and Antoku et al. Biochem. Biophys. Res. Comm. 286 (2001), 1003-1010. The Hsp and Bag antigen-binding sites can be obtained by any means, for example from a monoclonal antibody, or from a library of random combinations of and $V_L$ and $V_H$ domains. Preferably, said first and second binding domain bind to the C-terminal domain of the Hsp and Bag protein, respectively; see also Table 1 in the appended examples.

The term "bispecific molecule" includes molecules which have at least the two mentioned binding domains directly or indirectly linked by physical or chemical means. However, the bispecific molecule of the present invention may comprise further functional domains such as additional binding domains and/or moieties such as a cytotoxic agent or a label and the like. Means and methods for the preparation of multivalent, multispecific molecules having at least one specificity for a desired antigen are known to the person skilled in the art. For example, WO99/59633 describes multimeric molecules with at least one specificity for the HLA class II invariant chain (Ii) and their use for the clearance of therapeutic or diagnostic agents, autoantibodies, anti-graft antibodies, and other undesirable compounds. As used herein, unless otherwise indicated or clear from the context, antibody or binding domains, regions and fragments are accorded standard definitions as are well known in the art; see, e.g., Abbas et al., Cellular and Molecular Immunology (1991), W. B. Saunders Company, Philadelphia, Pa.

Bispecific molecules of the invention can cross-link antigens on target cells with antigens on immune system effector cells. This can be useful, for example, for promoting immune responses directed against cells which have a particular antigens of interest on the cell surface. According to the invention, immune system effector cells include antigen specific cells such as T cells which activate cellular immune responses and nonspecific cells such as macrophages, neutrophils and natural killer (NK) cells which mediate cellular immune responses. Hence, bispecific molecules of the invention can have a further binding site for any cell surface antigen of an immune system effector cell. Such cell surface antigens include, for example, cytokine and lymphokine receptors, Fc receptors, CD3, CD16, CD28, CD32, CD64 and CD94. In general, antigen binding sites are provided by scFvs which are derived from antibodies to the aforementioned antigens and which are well known in the art. Antigen-binding sites of the invention which are specific for cytokine and lymphokine receptors can also be sequences of amino acids which correspond to all or part of the natural ligand for the receptor. For example, where the cell-surface antigen is an IL-2 receptor, an antigen-binding protein of the invention can have an antigen-binding site which comprises a sequence of amino acids corresponding to IL-2. Other cytokines and lymphokines include, for example, interleukins such as interleukin-4 (IL-4), interleukin-5 (IL-5) and interleukin-15 (IL-15), and colony-stimulating factors (CSFs) such as granulocyte-macrophage CSF (GM-CSF), and granulocyte CSF (G-CSF).

In addition, any one of the described bispecific molecules may contain a binding domain binding FcgammaRI on activated effector cells. The clinical potential of this approach for the treatment of tumors such as B cell malignancies looks most attractive. Triggering of antitumor immunity by expression of anti-FcgammaR scFv on cancer cell surface has been described by Gruel et al., Gene Ther. 8 (2001), 1721-1728.

In addition or alternatively, the bispecific molecule of the invention may comprise a binding domain binding CD3. This embodiment is particularly useful for the treatment of carcinoma; see, e.g., Riesenberg et al., J. Histochem. Cytochem. 49 (2001), 911-917, which report on the lysis of prostate carcinoma cells by trifunctional bispecific antibodies (alpha EpCAM×alpha CD3).

These and other combinations of functional domains in the bispecific molecule of the present invention and uses thereof are encompassed by the present invention.

General strategies for preparation of multispecific molecules are known in the art; see; e.g., Tomlinson et al., Methods Enzymol. 326 (2000), 461-479. For example, intermediate molecular weight recombinant bispecific and trispecific antibodies by efficient heterodimerization of single chain variable domains through fusion to a Fab-chain are described in Schoonjans et al., Biomol. Eng. 17 (2001), 193-202. Dimeric and trimeric antibodies with high avidity for cancer targeting are described in Kortt et al., Biomol. Eng. 18 (2001), 95-108. All the means, methods and applications described in the mentioned publications can be applied and adapted to the bispecific molecule of the present invention and used in accordance with teaching disclosed herein.

Once a bispecific molecule has been produced in accordance with the present invention, various assays are available to demonstrate dual or multivalent specificity of the bispecific molecules of the invention such as direct and quantitative binding assays; see, e.g., WO94/13804, WO01/80883, WO01/90192 and the mentioned publications. Biologically active bispecific molecules, for example those supposed to have anti-tumor effect can be tested in well known in vitro test set-ups and also in mouse-tumor models; see review in Beun et al., Immunol. Today 21 (1994), 2413.

Preferably, the bispecific molecule of the present invention is a bispecific immunoglobulin, wherein the first binding domain is a first immunoglobulin variable region, and the second binding domain is a second immunoglobulin variable region recognizing Hsp and Bag, respectively. Such immunoglobulin variable regions can be obtained from polyclonal or monoclonal antibodies as well as from phage display and other screening techniques for immunoglobulin like binding proteins. As mentioned, antibodies can be monoclonal antibodies, polyclonal antibodies but also synthetic antibodies as well as fragments of antibodies, such as Fab, Fv or scFv fragments etc. Antibodies or fragments thereof can be obtained by using methods which are described, e.g., in Harlow and Lane "Antibodies, A Laboratory Manual", CSH Press, Cold Spring Harbor, 1988 or EP-A 0 451 216 and references cited therein. For example, surface plasmon resonance as employed in the BIAcore system can be used to increase the efficiency of phage antibodies which bind to an epitope of Hsp or Bag (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735.

Polyclonal and monoclonal antibodies against Hsp and Bag are described in the background section and in the appended examples. A particularly suitable source for anti-Hsp70 antibodies and binding domains are monoclonal antibody cmHsp70.1 as produced by hybridoma cmHsp70.1, deposited with the DSMZ-Deutsche Sammlung von Mikroorganismen und Zellkulturen GmbH, Mascheroder Weg 1b, D-38124 Braunschweig, Germany on Nov. 14, 2003, and assigned Accession Number DSM ACC2629, and cmHsp70.2 as produced by the hybridoma cmHsp70.2, deposited with the DSMZ-Deutsche Sammlung von Mikroorganismen und Zellkulturen GmbH on Nov. 14, 2003, and assigned Accession Number DSM ACC2630. These antibodies as well as derivatives thereof are described in detail in applicant's co-pending application "Therapeutic and diagnostic anti-Hsp70 antibodies", filed on the same day as the present application, i.e. on Dec. 6, 2004, claiming priority from European patent application No. 03028144.8, the disclosure content of which is incorporated herein by reference.

As mentioned before, the bispecific molecule of the present invention can be a dimeric, multimeric or single chain molecule. In single chain bispecific molecules the binding domains, preferably Fv regions, are linked by a peptide linker, which allows the domains to associate to form a functional antigen binding site; see, e.g., WO88/09344, WO92/01047. Peptide linkers used to produce scFvs are flexible peptides selected to assure proper three-dimensional folding and association of the $V_L$ and $V_H$ domains and maintenance of target molecule binding-specificity. Generally, the carboxy terminus of the $V_L$ or $V_H$ sequence is covalently linked by such a peptide linker to the amino terminus of a complementary $V_H$ or $V_L$ sequence. The linker is generally 10 to 50 amino acid residues, but any length of sufficient flexibility to allow formation of the antigen binding site is contemplated. Preferably, the linker is 10 to 30 amino acid residues. More preferably the linker is 12 to 30 amino acid residues. Most preferably is a linker of 15 to 25 amino acid residues. Example of such linker peptides include three times (Gly-Gly-Gly-Gly-Ser).

In a preferred embodiment, the bispecific molecule of the present invention is a bispecific antibody. The bispecific antibodies may comprise Fc constant regions, for example for association of the polypeptide chains comprising the binding domains. In addition to providing for association of the polypeptide chains, Fc constant domains contribute other immunoglobulin functions. The functions include activation of complement mediated cytotoxicity, activation of antibody dependent cell-mediated cytotoxicity and Fc receptor binding. When antigen-binding proteins of the invention are administered for treatment or diagnostic purposes, the Fc constant domains can also contribute to serum halflife. The Fc constant domains can be from any mammalian or avian species. When antigen binding proteins of the invention are used for treatment of humans, constant domains of human origin are preferred, although the variable domains can be non-human. In cases where human variable domains are preferred, chimeric scFvs can be used. Further means and methods for the production of bispecific antibodies are described in the art; see, e.g., WO97/14719 which describes a process for producing bispecific or bivalent double head antibody fragments, which are composed of a binding complex containing two polypeptide chains, and WO01/80883. Furthermore, the bispecific molecules of the invention can be optimized in their avidity for antigen(s) while maintaining their ability to function as a natural antibody, including the ability to activate complement mediated cytotoxicity and antibody dependent cellular toxicity; see, e.g., WO01/90192.

The bispecific molecules of the present invention preferably have a specificity at least substantially identical to the binding specificity of the natural ligand or binding partner of the Hsp or Bag protein. A binding domain binding Hsp or Bag can have a binding affinity of at least $10^{-5}$ M, preferably higher than $10^{-7}$ M and advantageously up to $10^{-10}$ M. In a preferred embodiment, the bispecific molecule has an affinity of at least about $10^{-7}$ M, preferably at least about $10^{-9}$ M and most preferably at least about $10^{-11}$ M for either or both Hsp and Bag.

Furthermore, the present invention relates to a nucleic acid molecule or a composition of nucleic molecules encoding the bispecific molecule of the present invention. In particular, said nucleic acid molecules encode at least the binding domains, for example the variable region of an immunoglobulin chain of any one of the before described antibodies. The nucleic acid molecules are preferably operably linked to expression control sequences. Usually, the nucleic acid molecule(s) will be part of (a) vector(s), preferably expression vectors used conventionally in genetic engineering, for example, plasmids; see also the references cited herein. In addition, the present invention relates to a cell comprising the nucleic acid molecule or composition described above. The cell may be a prokaryotic host cell including gram negative as well as gram positive bacteria such as, for example, *E. coli, S. typhimurium, Serratia marcescens* and *Bacillus subtilis*, or a eukaryotic cell or cell line including yeast, higher plant, insect and preferably mammalian cells, most preferably NSO and CHO cells. In a particularly preferred embodiment said cell is a natural killer (NK) cell. Preferably, said cell is capable of expressing the bispecific molecule of the invention, for example such that the bispecific molecule or its subunits are secreted through the cell membrane. Suitable cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). The present invention also envisages cells, which express the bispecific molecule of the invention or its binding domains such that they are localized on the cell membrane. In this embodiment, the bispecific molecule of the invention or its binding domains may function as cell membrane receptors, for example for the attraction of complement cells.

The present invention also relates to a method for producing the bispecific molecule of the invention comprising cross-linking a first binding domain which binds Hsp and a second binding domain which binds Bag. Conventional techniques for the production of bispecific proteins, preferably antibody fragments, are known to person skilled in the art; see, e.g., WO98/04592 and references cited therein. Starting material such as intact antibodies can be obtained according to methods known in the prior art; see literature cited supra and Current Protocols in Immunology, Codigan et al. eds., John Wiley+Sons. It is also known from the art how to carry out the individual reaction and purification steps; see the example and, e.g., Brennan et al. Science 229 (1985), 81-83; Jung et al. Eur. J. Immunol. 21 (1991), 2491-2495.

The present invention also relates to a method for producing a bispecific molecule of the present invention comprising culturing the above described cell under appropriate conditions and isolating the bispecific molecule or portions thereof. A variety of chemical and recombinant methods have been developed for the production of bispecific and/or multivalent molecules such as antibody fragments. For review, see Holliger and Winter, Curr. Opin. Biotechnol. 4 (1993), 446-449; Carter et al., J. Hematotherapy 4 (1995), 463-470; Plückthun and Pack, Immunotechnology 3 (1997), 83-105. For example, bispecificity and/or bivalency has been accomplished by fusing two scFv molecules via flexible linkers, leucine zipper motifs, CHCL-heterodimerization, and by association of scFv molecules to form bivalent monospecific diabodies and related structures. Multispecificity or multivalency has been achieved by the addition of multimerization sequences at the carboxy or amino terminus of the scFv or Fab fragments, by using for example, p53, streptavidin and helix-turnhelix motifs. For example, by dimerization via the helix-turn-helix motif of an scFv fusion protein of the form (scFv1)-hingehelix-turn-helix-(scFv2), a tetravalent bispecific miniantibody is produced having two scFv binding sites for each of two target antigens. Production of IgG type bispecific antibodies, which resemble IgG antibodies in that they possess a more or less complete IgG constant domain structure, has been achieved by chemical cross-linking of two different IgG molecules or by co-expression of two antibodies from the same cell. Chemical cross-linking is described in, e.g., Merchant et al., Nat. Biotechnology 16 (1998), 677-681. Furthermore, the production of homogeneous population of bivalent, bispecific molecules that bind to one antigen at one end and to a second antigen at the other end are described; see, e.g., Colonna and Morrison, Nat. Biotechnology 15 (1997), 159-163. Further means and methods for the expression and purification of bispecific molecules such as bispecific recombinant antibody fragments derived from antibodies are known in the art; see, e.g., Dincq et al, Protein Expr. Purif. 22 (2001), 11-24.

Furthermore, the present invention relates to a composition comprising in one or more compartments, the bispecific molecule or chemical derivatives thereof, the nucleic acid molecule or above described composition or the cell of the invention. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition. Furthermore, the pharmaceutical composition may also be formulated as a vaccine, for example, if the pharmaceutical composition of the invention comprises a bispecific molecule described above for passive immunization.

Therapeutic or diagnostic compositions of the invention are administered to an individual in a therapeutically effective dose sufficient to treat or diagnose disorders as mentioned above. The effective amount may vary according to a variety of factors such as the individual's condition, weight, sex and age. Other factors include the mode of administration. The pharmaceutical compositions may be provided to the individual by a variety of routes such as by intracoronary, intraperitoneal, subcutaneous, intravenous, transdermal, intrasynovial, intramuscular or oral routes. In addition, co-administration or sequential administration of other agents may be desirable. A therapeutically effective dose refers to that amount of bispecific molecule of the invention sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

For use in diagnosis, a variety of techniques are available for labeling biomolecules, are well known to the person skilled in the art and are considered to be within the scope of the present invention. Such techniques are, e.g., described in Tijssen, "Practice and theory of enzyme immuno assays", Burden, R H and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology", Academic Press, London (1987), or in the series "Methods in Enzymology", Academic Press, Inc. There are many different labels and methods of labeling known to those of ordinary skill in the art. Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}P$ or $^{125}I$), biotin, digoxygenin, colloidal metals, chemi- or bioluminescent compounds (like dioxetanes, luminol or acridiniums).

Labeling procedures, like covalent coupling of enzymes or biotinyl groups, iodinations, phosphorylations, biotinylations, random priming, nick-translations, tailing (using terminal transferases) are well known in the art. Detection methods comprise, but are not limited to, autoradiography, fluorescence microscopy, direct and indirect enzymatic reactions, etc.

In addition, the above described compounds etc. may be attached to a solid phase. Solid phases are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing bispecific molecules of the invention on solid phases include but are not limited to ionic, hydrophobic, covalent interactions and the like. The solid phase can retain one or more additional receptor(s) which has/have the ability to attract and immobilize the region as defined above. This receptor can comprise a charged substance that is oppositely charged with respect to the reagent itself or to a charged substance conjugated to the capture reagent or the receptor can be any specific binding partner which is immobilized upon (attached to) the solid phase and which is able to immobilize the reagent as defined above.

Commonly used detection assays can comprise radioisotopic or non-radioisotopic methods. These comprise, inter alia, RIA (Radioisotopic Assay) and IRMA (Immune Radioimmunometric Assay), EIA (Enzym Immuno Assay), ELISA (Enzyme Linked Immuno Assay), FIA (Fluorescent Immuno Assay), and CLIA (Chemiluminescent Immune Assay). Other detection methods that are used in the art are those that do not utilize tracer molecules. One prototype of these methods is the agglutination assay, based on the property of a given molecule to bridge at least two particles.

The present invention also relates to a kit comprising a bispecific molecule of the invention. Such kits are useful for a variety of purposes including but not limited to forensic analyses, diagnostic applications, and epidemiological studies in accordance with the above described diseases and disorders. Such a kit would typically comprise a compartmentalized carrier suitable to hold in close confinement at least one container. The carrier would further comprise reagents for detection such as labeled antigen or enzyme substrates or the like.

As is described in the examples, it has surprisingly been found that Bag-4 is expressed and localized on the cell surface of tumor cells. Therefore, besides using the above described bispecific molecules of the invention, an antibody capable of recognizing membrane-bound Bag or a corresponding binding molecule, a nucleic acid molecule encoding said antibody or binding molecule, or a cell expressing said antibody or binding molecule can be used for the preparation of a composition for the detection, targeting and/or treatment of a tumor or an infectious disease. Preferably, the nucleic acid molecule encoding an antibody capable of recognizing membrane-bound Bag or a corresponding binding molecule is in a form suitable for expression of the bispecific molecule on the cell surface for the preparation of a pharmaceutical composition for the targeting of a cell to a tumor cell or to a cell infected by a pathogen.

Accordingly, the embodiments described with respect to the bispecific molecule of the invention can also be applied to antibodies and other molecules capable of recognizing membrane-bound Bag such as, for example, bi- or multispecific molecules which comprise a first binding domain recognizing an epitope of Bag displayed on the cell surface, and a further functional domain, for example a binding domain capable of binding to a cell of the immune system and/or comprising a cytotoxic molecule or label as described herein.

As described before, the compositions of the present invention are useful in diagnosis, prophylaxis, vaccination or therapy. Accordingly, the present invention relates to the use of the bispecific molecule, the nucleic acid molecule or composition or the cell of the present invention for the preparation of a pharmaceutical or diagnostic composition for the treatment of diseases related to a disorder of the immune response, preferably for the treatment of infectious diseases, sepsis, diabetes or for the treatment of tumors. Preferably, the tumor to be treated or diagnosed is selected from the group consisting of glioblastoma, medulloblastoma, astrocytoma, primitive neuroectoderma, brain stem glioma cancers, colon carcinoma, bronchial carcinoma, squamous carcinoma, sarcoma, carcinoma of colon, cervix or pancreas, carcinoma in the head/neck, T cell lymphoma, B cell lymphoma, mesothelioma, leukemia, melanoma, gynecological tumors such as prostate, and meningeoma.

For these embodiments, the bispecific molecules or anti-Bag antibodies of the invention can be chemically or biosynthetically linked to anti-tumor agents or detectable signal-producing agents; see also supra. Antitumor agents linked to a bispecific molecule, for example a bispecific antibody, include any agents which destroy or damage a tumor to which the anti-body has bound or in the environment of the cell to which the antibody has bound. For example, an anti-tumor agent is a toxic agent such as a chemotherapeutic agent or a radioisotope. Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin. The chemotherapeutic agents are conjugated to the antibody using conventional methods; see, e.g., Hermentin and Seiler, Behring Inst. Mitt. 82 (1988), 197-215. Detectable signal-producing agents are useful in vivo and in vitro for diagnostic purposes. The signal producing agent produces a measurable signal which is detectable by external means, usually the measurement of electromagnetic radiation. For the most part, the signal producing agent is an enzyme or chromophore, or emits light by fluorescence, phosphorescence or chemiluminescence. Chromophores include dyes which absorb light in the ultraviolet or visible wavelength range, and can be substrates or degradation products of enzyme catalyzed reactions.

The invention further contemplates bispecific molecules of the invention to which target or reporter moieties are linked. Target moieties are first members of binding pairs. Anti-tumor agents, for example, are conjugated to second members of such pairs and are thereby directed to the site where the antigen-binding protein is bound. A common example of such a binding pair is adivin and biotin. In a preferred embodiment, biotin is conjugated to an bispecific molecule of the invention, and thereby provides a target for an anti-tumor agent or other moiety which is conjugated to avidin or streptavidin. Alternatively, biotin or another such moiety is linked to a bispecific molecule of the invention and used as a reporter, for example in a diagnostic system where a detectable signal-producing agent is conjugated to avidin or streptavidin. Suitable radioisotopes for use as anti-tumor agents are also known to those skilled in the art. For example, $^{131}$I or $^{211}$At is used. These isotopes are attached to the antibody using conventional techniques; see, e.g., Pedley et al., Br. J. Cancer 68 (1993), 69-73. Alternatively, the anti-tumor agent which is attached to the antibody is an enzyme which activates a prodrug. In this way, a prodrug is administered which remains in its inactive form until it reaches the tumor site where it is converted to its cytotoxic form once the antibody complex is administered. In practice, the antibody-enzyme conjugate is administered to the patient and allowed to localize in the region of the tissue to be treated. The prodrug is then administered to the patient so that conversion to the cytotoxic drug occurs in the region of the tissue to be treated. Alternatively, the anti-tumor agent conjugated to the antibody is a cytokine such as interleukin-2 (IL-2), interleukin-4 (IL-4), interleukin-15 (IL-15) or tumor necrosis factor alpha (TNF-α). The antibody targets the cytokine to the tumor so that the cytokine mediates damage to or destruction of the tumor without affecting other tissues. The cytokine is fused to the antibody at the DNA level using conventional recombinant DNA techniques.

As mentioned before, the above described embodiments also apply to the use of antibodies specifically recognizing membrane-bound Bag protein, preferably Bag-4, and molecules comprising a corresponding binding domain as well as nucleic acid molecules encoding such antibodies or molecules, cells transformed therewith and compositions comprising anyone of those components.

The present invention further provides methods of treating a mammal having an undesirable condition associated with a disease as defined above, comprising administering to the mammal a therapeutically effective dose of any one of the above described bispecific molecules or antibodies of the invention.

Compositions comprising the bispecific molecule of this invention or a compound capable of recognizing membrane-bound Bag can be added to cells in culture (in vitro) or used to treat patients, such as mammals (in vivo). Where the bispecific molecule are used to treat a patient, the bispecific molecule is preferably combined in a pharmaceutical composition with a pharmaceutically acceptable carrier such as a larger molecule to promote stability or a pharmaceutically acceptable buffer that serves as a carrier for the bispecific molecule that has more than one unit coupled to a single entity. The methods of the invention include administering to a patient, preferably a mammal, and more preferably a human, the composition of the invention in an amount effective to produce the desired effect. The bispecific molecule can be administered as a single dose or in multiple doses. Useful dosages of the active agents can be determined by comparing their in vitro activity and the in vivo activity in animal models. For example, methods of ex vivo immunization using heterologous intact bispecific and/or trispecific antibodies are described in EP-A-885 614 and induction of a long-lasting antitumor immunity by a trifunctional bispecific antibody is reported in Ruf and Lindhofer, Blood 98 (2001), 2526-2534.

Methods for extrapolation of effective dosages in mice, and other animals, to humans are known in the art. The present invention also provides a method of modulating (e.g., activating or inhibiting) immune cell (e.g., T-cells, B-cells, NK cells, LAK cells, or dendritic cells) activation, proliferation, and/or differentiation that includes contacting an immune cell with a bispecific molecule described above.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of a neoplastic or infectious disease. Most preferably, said subject is a human.

As mentioned before, it was found that an Hsp70 membrane-positive phenotype was associated with Bag-4 cell surface localization. Following sublethal γ-irradiation both molecules were found to be up-regulated in carcinoma cells with an initially low Hsp70 membrane expression. Functionally, an Hsp70/Bag-4 positive phenotype conferred protection against irradiation-induced effects including G2/M arrest and growth inhibition.

Accordingly, in another embodiment the present invention relates to a method for diagnosing a radiation therapy resistant neoplastic disorder or infectious disease of a patient comprising assaying membrane-bound Bag and/or co-localization of Hsp and Bag protein on the cell surface of neoplastic cells in a sample from the patient, wherein the presence or increased amount of membrane-bound Bag and/or co-localized Hsp and Bag protein is indicative for the disorder. The presence of Bag/Hsp complex can be assayed in primary tumor tissue by means such as coimmunoprecipitation with antibodies to Bag and hsp70, similar to the method of detecting tumors containing complexes of p53 and Hsp70 described in U.S. Pat. No. 5,652,115. Samples taken from patients for use in the detecting steps described herein are generally biological fluids such as serum, blood plasma, or ascites fluid. Serum and blood plasma, particularly serum, is preferred.

On the other hand a strong Hsp70/Bag-4 membrane expression provides a target recognition structure for the cytolytic attack mediated by NK cells. Thus, in a further embodiment the present invention relates to the use of NK cells or an activator of NK cells for the preparation of a pharmaceutical composition for the treatment of a tumor or infectious disease in a patient which has been positively tested according to the diagnostic method described above. Said NK cells may be activated prior to administration to the patient or can be designed to be administered in conjunction with an activator of NK cells. Preferably, said activator comprises a peptide of Hsp70 and/or a peptide of Bag protein. Methods for activating NK cells by the use of Hsp70 protein or fragments thereof and the medical applications of the products so obtained, such as pharmaceuticals, medicinal products or medicinal adjuvants containing Hsp70 protein or fragments thereof or activated NK cells are described in WO99/49881. Furthermore, immunostimulatory peptides derived from Hsp70 protein and the use of such peptides for the stimulation of natural killer cell (NK cell) activity are disclosed in WO02/22656. Another method for sensitizing antigen-presenting cells and membrane vesicles with immunogenic properties, and their use for vectoring and presenting antigens in vitro or in vivo and methods or compositions for treating cancers, infectious, parasitic or autoimmune diseases in particular are described in WO99/03499.

The methods described in the mentioned international applications for stimulating of NK cells can be easily adapted to the uses and methods of the present invention.

As mentioned before, it has been found that Hsp70/Bag-4 membrane expression provides a target recognition structure for the cytolytic attack mediated by NK cells. Accordingly, it is reasonable to assume that Bag protein, especially Bag-4, can be used to elicit a strong immune response against undesired cells, such as tumor cells which, for example, by use of targeted Bag expression on their cell surface display a recognition structure for NK cells. Thus, in a still further embodiment the present invention relates to the use of Bag protein or fragment thereof or an agent mimicking membrane-bound Bag in association with Hsp for the preparation of a pharmaceutical composition for inducing and/or enhancing a cytolytic attack of NK cells against undesired cells. Bag proteins are described, for example, in Antoku et al., Biochem. Biophys. Res. Commun. 286 (2001), 1003-1010.

Said agent can be for example any agent which induces or enhances the expression and/or localization of Bag on the cell surface of said undesired cell. Preferably, said agent or a combination of agents induce or enhance concomitantly the expression and/or co-localization of Hsp and Bag on the cell surface of a tumor cell. This also includes γ-irradiation; see also the examples. Said agent can also be comprised of at least one of the following: Hsp70 and/or Bag-4 polypeptides or fragments thereof, cells expressing Hsp70 in association with Bag-4 on their cell surface, the membrane-fraction of cells expressing Hsp70 in association with Bag-4 on their cell surface and/or anti-idiotypic antibodies of membrane-bound Hsp70 in association with Bag-4.

Furthermore, said pharmaceutical composition may additionally contain at least one compound which enhances an immune response; see also supra. Preferably, said undesired cells to be treated are tumor cells.

In another embodiment the present invention relates to a method for the preparation of an agent mimicking membrane-bound Hsp70 in association with Bag-4 comprising the following steps:
(a) raising antibodies specific for membrane-bound Hsp70 in association with Bag-4; and
(b) raising anti-idiotypic antibodies by using the antibodies of step (a) or at least part of the variable region thereof as an antigen.

One concept for immune therapy of cancer involves induction of antigen mimic antibodies to trigger the immune system into a response against the tumor cells. Anti-idiotypic antibodies (Ab2) directed against the antigen-combining site of other antibodies (Ab1) may functionally and even structurally mimic antigen and induce anti-anti-idiotypic immune response. An example of functional mimicry of an anti-idiotypic antibody to a murine monoclonal immunoglobulin (Ab1), which defines ovarian cancer antigen CA125, is described in Ma et al., Jpn. J. Cancer Res. 93 (2002), 78-84. A murine monoclonal anti-idiotypic antibody as a surrogate antigen for human Her-2/neu is described in Baral et al., Int. J. Cancer 92 (2001), 88-95. Further examples comprise active immunotherapy with anti-idiotypic antibody for patients with nasopharyngeal carcinoma (NPC), described by Li et al., Cancer Biother. Radiopharm. 17 (2002), 673-679 and anti-idiotypic antibodies carrying the "internal image" of peptide YIGSR inhibit spontaneous metastasis of Lewis lung carcinoma in mice described by Koliakos et al. in In Vivo 16 (2002), 511-518. Preferably, the anti-idiotypic antibody is humanized; see also supra.

As described in the examples, the Hsp70/Bag-4 positive phenotype conferred protection against irradiation-induced affects and thus renders the corresponding tumor treatment less or even ineffective. Therefore, it is expected that inhibition of the co-localization of Hsp and Bag and/or interaction of both proteins reverse the irradiation-resistant genotype of the tumor cells. Accordingly, in a further aspect the present invention relates to the use of an inhibitor of the association of membrane-bound Hsp70 with a member of the anti-apoptotic Bcl-2-associated athanogene (Bag) family for the preparation of a pharmaceutical composition for the treatment of a tumor.

The terms "antagonist/inhibitor" in accordance with the present invention include chemical agents that modulate the action of Bag inconjunction with Hsp or vice versa, either through altering its enzymatic or biological activity or through modulation of expression, e.g., by affecting transcription or translation. In some cases the antagonist/inhibitor may also be a substrate or ligand binding molecule.

The term "inhibitor" includes both substances which reduce the activity of the Bag protein and those which nullify it altogether. Antagonists include competitive as well as non-competitive antagonists. A competitive antagonist (or competitive blocker) interacts with or near the site of Bag specific for Hsp binding. A non-competitive antagonist or blocker inactivates the function of Bag by interacting with a site other than the Hsp interaction site. Preferably, the antagonist/inhibitor of the interaction of Bag and Hsp are small chemical agents which directly interact with Hsp and/or Bag. Therefore, there will preferably be a direct relationship between the molar amount of compound required to inhibit membrane association of Hsp and Bag and the molar amount of Bag and/or Hsp present or lacking on the cell surface. Antagonists may be peptides, proteins, nucleic acids, antibodies, small organic compounds, peptide mimics, aptamers or PNAs (Milner, Nature Medicine 1 (1995), 879-880; Hupp, Cell 83 (1995), 237-245; Gibbs, Cell 79 (1994), 193-198; Gold, Ann. Rev. Biochem. 64 (1995), 736-797). For the preparation and application of such compounds, the person skilled in the art can use the methods known in the art, for example those referred to herein.

According to a preferred embodiment, said inhibitor binds to the ATPase domain of Hsp and/or to the corresponding binding domain of Bag. Dissection of the ATP-binding domain of the chaperone hsc70 for interaction with the cofactor Hap46 is described in Petersen et al., J. Biol. Chem. 276 (2001), 10178-10184, by using (i) screening of membrane-bound peptide libraries based on the sequence of the ATP-binding domain and (ii) the phage-display technique with random dodecapeptides. These approaches can also be used in accordance with the present invention.

In a further preferred embodiment of the present invention said inhibitor is an antibody, as disclosed above.

The antibodies which are of use in the present invention also can be made using non-human primates. General techniques for raising therapeutically useful antibodies in baboons can be found, for example, in WO91/11465 (1991) and Losman et al., Int. J. Cancer 46 (1990), 310. Alternatively, the antibodies can be "humanized" monoclonal antibodies. Humanized monoclonal antibodies are produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., Proc. Natl. Acad. Sci. USA 86 (1989), 3833. Techniques for producing humanized monoclonal antibodies are described, for example, by Jones et al., Nature 321 (1986), 522; Riechmann et al., Nature 332 (1988), 323; Verhoeyen et al., Science 239 (1988), 1534; Carter et al., Proc. Natl. Acad. Sci. USA 89 (1992), 4285; Sandhu, Crit. Rev. Biotech. 12 (1992), 437; and Singer et al., J. Immunol. 150 (1993), 2844.

Antibodies of the present invention also may be derived from human antibody fragments isolated from a combinatorial immunoglobulin library; see, for example, Barbas et al., Methods: A Companion To Methods In Enzymology, Vol. 2 (1991), page 119 and Winter et al., Ann. Rev. Immunol. 12 (1994), 433. Cloning and expression vectors that are useful for producing a human immunoglobulin phage library can be obtained, for example, from STRATAGENE Cloning Systems (La Jolla, Calif., USA).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described by Green et al., Nature Genet. 7 (1994), 13; Lonberg et al., Nature 368 (1994), 856; and Taylor et al., Int. Immunol. 6 (1994), 579.

All mentioned antibodies may additionally be linked to a toxic agent and/or to a detectable agent.

Alternatively, the present invention provides aptamers, which are directed against Hsp and/or Bag. Aptamers are DNA or RNA molecules that have been selected from random pools based on their ability to bind other molecules. Aptamers have been selected which bind nucleic acid, proteins, small organic compounds, and even entire organisms. Aptamers in the form of so called Spiegelmers have been described by Vater and Klussmann, Cur. Opin. Drug Disc. Devel. 6 (2003), 253-261.

All the above described diagnostic and medical uses are preferably applied to tumors and neoplastic cells which are resistant to radiation therapy. Different kinds of tumors which can be treated in accordance with the present invention are described above and in more detail further below.

As already mentioned, the Hsp70/Bag-4 positive phenotype confers protection against the otherwise cited toxic effects of γ-irradiation. With the use of an inhibitor of said co-localization and/or interaction of Hsp70 and Bag-4 on the cell surface of the given target cells it is expected that said target cells, particularly tumor cells and cells infected by a pathogen, can be sensitized again for the activity of cytotoxic agents such as γ-irradiation but also to anti-cancer drugs. Accordingly, in a further embodiment the present invention relates to the use of any one of the above described inhibitors as a first agent for the preparation of a pharmaceutical composition for sensitizing tumor cells for the activity of a cytotoxic second agent. This finding enables regimen to improve the effectiveness of chemotherapeutic agents which otherwise would be less effective or even not effective at all.

Thus, the present invention relates to the use of the above described inhibitors for sensitizing tumor cells and infected cells for the activity of cytotoxic approaches such as apoptosis induction by chemotherapeutic drugs, γ-irradiation, and triggering of death receptors such as the CD95; see also supra. In particular, the present invention relates to compositions, preferably pharmaceutical compositions, for sensitizing tumor cells, in particular cells that are positively tested for the presence of Bag and/or Hsp on their cell surface for the activity of chemotherapeutic agents.

Chemotherapy for tumors is varied, because there are so many different forms of this disease. Treatment may rely on a single anticancer medication—that is, single agent chemotherapy—or it may involve combination chemotherapy with a number of different anticancer drugs. Such drugs destroy cancer cells by preventing them from growing and dividing rapidly. In a preferred embodiment of the invention, said cytotoxic approaches induce apoptosis. An overview about apoptosis, the cell's intrinsic death program and key regulator of tissue homeostasis, is given in, e.g., Fulda and Debatin, Curr. Med. Chem. Anti-Canc. Agents 3 (2003), 253-262.

Many different chemotherapeutic plans are available for the treatment of including mechlorethamine, vincristine (Oncovin®), procarbazine, prednisone; doxorubicin (Adriamycin®), bleomycin, vinblastine, dacarbazine, chlorambucil (Leukeran®), procarbazine hydrochloride (Matulane®), vinblastine sulfate (Velban®) and etoposide (VP-16; VePesid®). Alternative chemotherapies comprise the use of agents such as bleomycin.

Furthermore, biological therapies are available. One of the biological therapies used for the treatment of cancer is interferon therapy. Interferons are a class of proteins that are released by virus-infected cells. They help normal cells to make antiviral proteins. Interferons also help the body to reduce tumor cell proliferation (growth and reproduction), while strengthening the body's immune response. Interferon-alpha (INFα) is a type of interferon that may be used to treat cancer.

Hence, in a preferred embodiment the present invention relates to the use of any one of the above described inhibitors for the treatment of the above described undesired cells by sensitizing target cells for the cytotoxic activity of a second agent such as staurosporine, mechlorethamine, vincristine, procarbazine, prednisone, doxorubicin, bleomycin, vinblastine, dacarbazine, chlorambucil, etoposide, mitoxantrone, genestein, phenoxodiol, interferons, drugs triggering death receptors such as the CD95, and pro-drugs and pharmaceutically acceptable salts of any one thereof. Those compounds can either be present in the same pharmaceutical composition as the inhibitor or in a separately be prepared for administration. In the latter, the pharmaceutical compositions are preferably being applicable simultaneously or sequentially. Preferably, said second agent is an apoptosis inducing agent. Most preferably, said second agent is a chemotherapeutic drug or γ-irradiation.

Said pharmaceutical composition comprising the molecules of the invention, e.g. an inhibitor as defined above, can be designed to be administered prior, during or after exposure of the tumor cells to γ-irradiation.

Infectious diseases that can be treated or prevented by the methods of the present invention are caused by infectious agents including, but not limited to, viruses, bacteria, fungi, protozoa and parasites. Bacterial diseases that can be treated or prevented by the methods of the present invention are caused by bacteria including, but not limited to, mycobacteria *rickettsia, mycoplasma, neisseria* and *legionella*. Protozoal diseases that can be treated or prevented by the methods of the present invention are caused by protozoa including, but not limited to, *leishmania, kokzidioa*, and *trypanosoma*. Parasitic diseases that can be treated or prevented by the methods of the present invention are caused by parasites including, but not limited to, *chlamydia* and *rickettsia*.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, carcinoma of the head/neck, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, and heavy chain disease.

In a specific embodiment the cancer is metastatic. In another specific embodiment, the subject having a cancer is immunosuppressed by reason of having undergone anti-cancer therapy (e.g., chemotherapy radiation) prior to administration of the compositions of the invention.

In a further embodiment, the present invention relates to a method for the identification of an anti-tumor agent comprising:
(a) providing a cell expressing Hsp70 and Bag-4 on its cell surface;
(b) treating said cell with at least one candidate compound; and
(c) determining whether said candidate compound interferes with the association of Hsp70 and Bag-4 on the cell surface of the cell.

The assays may be simple "yes/no" assays to determine whether there is a change in expression, function or interaction, or may comprise any one of the above described methods, for example for the detection of resistance against γ-irradiation. The assay may be made quantitative by comparing the expression or function of a test sample with the levels of expression or function in a standard sample. Modulators identified in this process are useful as therapeutic agents.

The assay methods of the present invention can be in conventional laboratory format or adapted for high throughput. The term "high throughput" (HTS) refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well, 384-well or more-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

The test substances which can be tested and identified according to a method of the invention may be expression libraries, e.g., cDNA expression libraries, peptides, proteins, nucleic acids, antibodies, small organic compounds, hormones, peptidomimetics, PNAs, aptamers or the like (Milner, Nature Medicine 1 (1995), 879-880; Hupp, Cell 83 (1995), 237-245; Gibbs, Cell 79 (1994), 193-198 and references cited supra). The test substances to be tested also can be so called "fast seconds" of known drugs. The invention also relates to further contacting the test cells with a second test substance or mixture of test substances in the presence of the first test substance.

In the method of the invention, said cells are preferably contained in a container, for example in a well in a microtiter plate, which may be a 24, 96, 384 or 1586 well plate. Alternatively, the cells can be introduced into a microfluidics device, such as those provided by Caliper (Newton, Mass., USA). In another preferred embodiment, step (b) of the method of the present invention comprises taking 2, 3, 4, 5, 7, 10 or more measurements, optionally at different positions within the container. In some embodiments of the method of the present invention, a compound known to activate or inhibit the target gene or gene product is added to the medium prior to step (b).

Preferably, in a first screen said test substance is comprised in and subjected as a collection of compounds. Said collection of compounds may have a diversity of about $10^3$ to about $10^5$. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Drug discovery by dynamic combinatorial libraries is described, for example, in Nat. Rev. Drug Discov. 1 (2002), 26-36 and Drug Discov. Today 7 (2002), 117-125.

Furthermore, the above described methods can, of course, be combined with one or more steps of any of the above described screening methods or other screening methods well known in the art. Methods for clinical compound discovery comprises for example ultrahigh-throughput screening (Sundberg, Curr. Opin. Biotechnol. 11 (2000), 47-53) for lead identification, and structure-based drug design (Verlinde and Hol, Structure 2 (1994), 577-587) and combinatorial chemistry (Salemme et al., Structure 15 (1997), 319-324) for lead optimization. Once a drug has been selected, the method can have the additional step of repeating the method used to perform rational drug design using the modified drug and to assess whether said modified drug displays better affinity according to for example interaction/energy analysis. The method of the present invention may be repeated one or more times such that the diversity of said collection of compounds is successively reduced.

Substances are metabolized after their in vivo administration in order to be eliminated either by excretion or by metabolism to one or more active or inactive metabolites (Meyer, J. Pharmacokinet. Biopharm. 24 (1996), 449-459). Thus, rather than using the actual compound or drug identified and obtained in accordance with the methods of the present invention a corresponding formulation as a pro-drug can be used which is converted into its active form in the patient by his/her metabolism. Precautionary measures that may be taken for the application of pro-drugs and drugs are described in the literature; see, for review, Ozama, J. Toxicol. Sci. 21 (1996), 323-329.

Furthermore, the present invention relates to the use of a compound identified, isolated and/or produced by any of these methods for the preparation of a composition for the treatment of tumors or infectious diseases. As a method for treatment the identified substance or the composition containing it can be administered to a subject suffering from such a disorder. Compounds identified, isolated and/or produced by the method described above can also be used as lead compounds in drug discovery and preparation of drugs or pro-drugs.

This usually involves modifying the lead compound or a derivative thereof or an isolated compound as a to achieve (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmakinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetates, or (xiv) N-acetylation to amides, phenylcarbamates, or (xv) synthesis of Mannich bases, imines, or (xvi) transformation of ketones or aldehydes to Schiffs bases, oximes, acetates, ketales, enolesters, oxazolidines, thiozolidines or combinations thereof; and (b) formulating the product of said modification with a pharmaceutically acceptable carrier.

The various steps recited above are generally known in the art. For example, computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, peptidomimetics and/or computer aided design of appropriate derivatives and analogues can be used, for example, according to the methods described above.

Methods for the lead generation in drug discovery also include using proteins and detection methods such as mass spectrometry (Cheng et al. J. Am. Chem. Soc. 117 (1995), 8859-8860) and some nuclear magnetic resonance (NMR) methods (Fejzo et al., Chem. Biol. 6 (1999), 755-769; Lin et al., J. Org. Chem. 62 (1997), 8930-8931). They may also include or rely on quantitative structure-action relationship (QSAR) analyses (Kubinyi, J. Med. Chem. 41 (1993), 2553-2564, Kubinyi, Pharm. Unserer Zeit 23 (1994), 281-290) combinatorial biochemistry, classical chemistry and others (see, for example, Holzgrabe and Bechtold, Pharm. Acta Helv. 74 (2000), 149-155). Furthermore, examples of carriers and methods of formulation may be found in Remington's Pharmaceutical Sciences.

Once a drug has been selected in accordance with any one of the above described methods of the present invention, the drug or a pro-drug thereof can be synthesized in a therapeutically effective amount. As used herein, the term "therapeutically effective amount" means the total amount of the drug or pro-drug that is sufficient to show a meaningful patient benefit, i.e., treatment, healing, prevention or amelioration of a condition related to a tumor or infectious disease, or an increase in rate of treatment, healing, prevention or amelioration of such conditions. In addition or alternatively, in particular with respect to pre-clinical testing of the drug the term "therapeutically effective amount" includes the total amount of the drug or pro-drug that is sufficient to elicit a physiological response in a non-human animal test.

The invention also provides kits for carrying out the diagnostic methods and/or therapeutic regimens of the invention. Such kits comprise in one or more containers an anti-Hsp and/or anti-Bag antibody; and optionally suitable means for detection.

Most embodiments have generally been described for Bag proteins. Since, however, specifically Bag-4 has been determined on tumor cells embodiments are preferred in accordance with the present invention, wherein said Bag protein is Bag-4. Most preferably, said Bag protein or fragment thereof comprises at least one epitope of the C-terminal localized BAG domain.

As already mentioned before, experiments performed in accordance with the present invention for the first time demonstrated the expression of Bag on the cell surface of target cells, particularly on tumor cells. Therefore, molecules which recognize Bag protein, in particular an epitope of the C-terminal localized BAG domain, can be used for the diagnosis and targeting of diseased cells which express Bag on their cell surface.

Thus, in a further aspect the present invention relates to the use of an antibody specifically recognizing membrane-bound Bag protein or a binding domain thereof for the detection and/or treatment of a tumor or an infectious disease. Preferably, said antibody or binding domain bind to an epitope of the C-terminal localized BAG domain. Most preferably, said Bag protein is Bag-4.

Hence, as also discussed previously, all embodiments disclosed with respect to the bispecific molecules of the invention are applied to the use of said anti-Bag antibody or corresponding binding molecules as well. For example, said anti-Bag antibody or binding domain can comprise further functional domains such as those described hereinbefore, i.e. foreign binding domains and/or cytotoxic agents or labels. The sources for such anti-Bag antibodies and means for their preparation have also been discussed before.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. Particularly useful means and methods for the recombinant production of bispecific molecules are described in WO94/13804, WO01/80883 and WO01/90192. All references mentioned herein are incorporated in their entirety.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Experimental Procedures

Cells and Cell Culture

The human colon carcinoma sublines CX+, and CX−, generated from the parental cell line CX2 (Tumorzellbank, DKFZ Heidelberg, Germany) by cell sorting, using the mouse anti-human Hsp70-specific monoclonal antibody (C-terminus, $aa_{450-463}$, clone cmHsp70.1, multimmune GmbH, Regensburg, Germany), were cultured in RPMI 1640 medium (Gibco, Eggenstein, Germany) supplemented with 10% heat-inactivated FCS (Gibco), 1% antibiotics (penicillin/streptomycin, Gibco), 2 mM L-glutamine (Gibco). The human pancreas carcinoma sublines Colo+ and Colo− were sorted from the original cell line Colo 357 (CAMR Centre for Applied Microbiology & Research, Salisbury, Wiltshire, U.K.) following the protocol described for CX+/CX− cells (Multhoff et al., J. Immunol. 158 (1997), 4341-4350). Growth conditions of pancreas and colon carcinoma sublines were comparable. Exponential cell growth was maintained by regular cell passages. Every 3 days cells were trypsinized for 1 min with trypsin/EDTA (Gibco) and single cell suspensions were seeded at a constant cell density of $0.5 \times 10^6$ cells in 5 ml medium in T25 ventilated small culture flasks (Greiner, Nuertingen, Germany).

The human cervix carcinoma cell line HeLa was stably transfected either with an expression vector harboring mouse Bag-4 cDNA (pcDNA-SODD, access code Q8CI61) or with the corresponding control vector (neo). Eight micrograms of DNA were electroporated into $5 \times 10^6$ cells using a BioRad gene pulser (750 V, 25 µF, 200 Ohm, 0.4 cm cuvettes), and cells were selected in G418 (0.3 mg/ml, Calbiochem, San Diego, Calif., U.S.A.) containing medium (Eichholtz-Wirth et al., Cancer Lett. 194 (2003), 81-89). Individual subclones stably overexpressing mouse Bag-4, were isolated and cultured, as described above.

Plating efficiency, doubling time and protein content in Hsp70 high- and low-expressing CX+/CX−, Colo+/Colo− and HeLa Bag-4/HeLa neo cells were comparable under physiological conditions.

γ-Irradiation

Exponentially growing, carcinoma cells were exposed to γ-irradiation, delivered by a $^{137}$Cs source at a dose rate of 1 Gy per 10 sec, on day 2 following cell passage, either fractionated (2×2 Gy to 5×2 Gy), or with single doses of 1×10 Gy and 1×20 Gy. Cell viability was determined in the adherent and non-adherent cell population by trypan blue exclusion assays using light microscopy and by Annexin-V FITC staining on a flow cytometer (FACSCalibur, Becton Dickinson, Heidelberg, Germany).

SDS-PAGE and Western Blot Analysis

Cell pellets ($1.0 \times 10^6$ cells) were washed in PBS and solubilized in lysis buffer (120 mM sodium chloride, 40 mM Tris pH 8.0, 0.5% NP40). Proteins were denatured in sample buffer (25 mM Tris hydrochloride pH 6.8, 2% SDS, 10% glycerol, 10% mercaptoethanol, and bromphenol blue) by boiling for 10 min. Equal protein amounts (10 µg) were administered to 10% SDS-PAGE under reducing conditions (Laemmli, Nature 227 (1970), 680-685). After electrophoresis proteins were transferred onto nitrocellulose membranes and blotted according to a protocol of Towbin (Towbin et al., Proc. Natl. Acad. Sci. U.S.A. 76 (1979), 4350-4354). The following antibodies, diluted 1:1000 were used for Western blotting (Table 1):

TABLE 1

List of antibodies used for Western blot analysis (W), flow cytometry (F), immuno-histochemistry (I), and antibody blocking studies (B).

| Antibody | Specificity | recognition site | assay |
|---|---|---|---|
| cmHsp70.1 monoclonal | Hsp70 | C-terminus, $aa_{454-461}$ | W, F, I, B |
| LR-1 monoclonal | Hsp70 | C-terminus, $aa_{450-463}$ | W, F, B |
| H-300 polyclonal | Bag-4 | C-terminus, $aa_{158-457}$ | W, F, I, B |
| N-19 polyclonal | Bag-4 | N-terminus | W, F, B |
| IMG-152 polyclonal | Bag-4 | C-terminus, $aa_{443-457}$ | W, F, B |
| C-16 polyclonal | Bag-1 | C-terminus | W, F |
| FL-274 polyclonal | Bag-1 | Full length, $aa_{1-274}$ | W, F |

The sources of the antibodies were as follows: mouse anti-human Hsp70 (C-terminus, $aa_{450-463}$, clone cmHsp70.1, multimmune GmbH, Regensburg, Germany), rabbit anti-human Bag-4/SODD (C-terminus, H-300; Santa Cruz Biotechnology, Santa Cruz, Calif., U.S.A.), rabbit anti-human Bag-4/SODD (C-terminus, $aa_{443-457}$, IMG-152, Imgenex, San Diego, U.S.A.), goat anti-human Bag-4/SODD (N-terminus, N19; Santa Cruz Biotechnology), goat anti-human Bag-1 (C-terminus; C-16, Santa Cruz Biotechnology), rabbit anti-human Bag-1 (full length; FL-274, Santa Cruz Biotechnology), mouse anti-human tubulin (clone DM1A, Oncogene, Boston, U.S.A.). After incubation with the corresponding horseradish peroxidase-conjugated secondary antibodies (DAKO, Glostrup, Denmark), also diluted 1:1000, protein bands were visualized by chemiluminescence (ECL detection-kit, Amersham Biosciences, Little Chalfont, U.K.). Autoradiographs were recorded on X-omat films (Kodak, Stuttgart, Germany). Pre-stained standard protein-markers (Amersham Biosciences) were used for estimating the molecular weights of each protein.

Flow Cytometry

Tumor cells were counted and $0.1 \times 10^6$ cells were incubated with a FITC-conjugated Hsp70 monoclonal antibody (clone cmHsp70.1, multimmune GmbH) for 15 min at 4° C. Following washing in PBS/10% heat-inactivated FCS, cells were incubated with one of the following Bag-specific antibodies: Bag-4 (H-300, N-19, Santa Cruz Biotechnology; and IMG-152, Imgenex), Bag-1 (C-16, FL-274, Santa Cruz Biotechnology) for another 15 min. After incubation with corresponding PE-conjugated secondary antibodies for 15 min, followed by a second washing step, 7-amino-actinomycin D (7-AAD, Becton Dickinson Pharmingen, Heidelberg, Germany)-negative, viable cells were analysed on a FACSCalibur flow cytometer (Becton Dickinson).

Immunofluorescence Microscopy

Tumor cells were stained with Hsp70- (clone cmHsp70.1 or LR-1, multimmune GmbH) and Bag-4 (IMG-152, Imgenex)-specific antibodies as described earlier and transferred to glass slides in Fluorescent Mounting Medium (DAKO, Carpinteria, U.S.A.). Slides were analysed on a Zeiss Axioscop 25 scanning microscope (Zeiss, Jena, Germany) equipped with a 100× (planar) and 63× (apochromatic) oil-immersion objective and standard filters. Images were treated by multiplicative shading correction using the software Axiovision (Zeiss Vision, Jena, Germany). Photographs of specifically stained sections were taken; the localization of Bag-4 was visualized in red (PE) and of Hsp70 in green (FITC). An overlap of red and green is indicated in yellow.

Light Microscopy

Either untreated or γ-irradiated ($1 \times 10$ Gy) carcinoma cells were analysed for transmission microscopy using a Zeiss Axiovert 25 scanning microscope (Zeiss) at a magnification of 10× and 40×.

$^3$H-Thymidine Incorporation Assay

Cells were seeded in T25 culture flasks and cultivated for 24 h. Then adherent cells were irradiated ($1 \times 10$ Gy), trypsinized and counted. Appropriate cell numbers (5 to $10 \times 10^3$ cells/well) were resuspended in culture medium (150 μl/well), plated into 96 well flat bottom plates, and incubated for another 24 h or 48 h, respectively in the presence of 1 μCi $^3$H-thymidine. Then $^3$H-thymidine uptake in the DNA of the cells was measured in a scintillation counter (Perkin Elmer Life Sciences, Boston, U.S.A.).

Cell Cycle Analysis

DNA-content was analysed in ethanol (80%) fixed untreated and irradiated ($1 \times 10$ Gy) carcinoma cells. Following a washing step in 1 mM EDTA/PBS and resuspension in PBS (1 ml), 10 μl propidium iodide solution (5 mg/ml) and 10 μl ribonuclease (10 μg/ml) were added. Cells were analysed on a flow cytometer (FACSCalibur, Becton Dickinson, Heidelberg, Germany) after an incubation period of 20 min at room temperature.

Cell Mediated Lympholysis Assay (CML)

NK cells were generated from heparinized blood (200 ml) of healthy human individuals, following Ficoll density gradient centrifugation and CD94 antibody-based magnetic bead cell sorting, according to the CD56 antibody standard protocol (MidiMACS; Miltenyi, Bergisch Gladbach, Germany). After a 4 day stimulation period with low dose IL-2 (100 IU/ml; Chiron) plus 2 μg/ml Hsp70 peptide TKD ($aa_{450-463}$; see WO02/22656) the cytolytic response was tested against Hsp70-high expressing CX+, Colo+ and HeLa Bag-4 and low expressing CX−, Colo−, HeLa neo cells, either untreated or following irradiation with 10 Gy and a recovery period of 24 h, in a standard $^{51}$Cr assay (MacDonald et al., J. Exp. Med. 140 (1974), 718-730). Briefly, different dilutions of effector and target cells (40:1 to 2:1) were co-incubated in duplicates for 4 h at 37° C., in a final volume of 200 μl. Then supernatants (30 μl) were collected and radioactivity was measured on a γ-counter (Topcount, Packard instrument). Antibody blocking studies were performed either with Hsp70− (clone cmHsp70.1), or Bag-4-specific antibodies (H-300; IMG-152), that are known to detect membrane-bound Bag-4. Therefore, $1 \times 10^6$ carcinoma target cells were incubated with the antibodies at a concentration of 10 μg/ml for 15 min after labeling.

The percentage specific lysis was determined according to the following equation: % lysis: experimental release−spontaneous release)/(maximum release−spontaneous release)× 100. Percentage spontaneous release of each target cell was less than 25%.

Miscellaneous

Chemicals were from Sigma (Munich, Germany), Merck (Darmstadt, Germany) or Roth (Karlsruhe, Germany), if not indicated otherwise.

Statistics

For statistical analysis Student's t-test was measured. A confidence level above 95% ($p<0.05$) was determined as significant.

Example 1

γ-Irradiation Induces an Increase in Membrane-Bound Hsp70 and Bag-4 in Initially Low Expressing Carcinoma Sublines By cell sorting of the parental CX-2 colon and Colo357 pancreas carcinoma cells, using Hsp70-specific monoclonal antibodies (Table 1), stably Hsp70-high (CX+: >80%; Colo+: >75%) and -low expressing (CX−: <30%; Colo−: <35%) carcinoma sublines were generated. To measure irradiation-induced effects the sublethal irradiation dose was defined. For that purpose, exponentially growing carcinoma sublines with initially different Hsp70 membrane expression pattern were γ-irradiated either fractionated (2×2 Gy and 5×2 Gy), or with single doses of 1×10 Gy and 1×20 Gy, respectively. Up to a total irradiation dose of 10 Gy, either after single or fractionated administration, followed by a recovery period of 24 h at 37° C., cell viability of colon and pancreas carcinoma sublines, as determined by trypan blue exclusion assays and Annexin-V stainings, remained unaffected. Following γ-irradiation at 1×20 Gy, cell viability of Hsp70-low expressing CX− and Colo− cells was reduced more pronounced as compared to that of Hsp70-high expressing CX+ and Colo+ tumor sublines (Table 2).

TABLE 2

Viability of tumor cells following single or fractionated γ-irradiation.

| carcinoma | control | 2 × 2 Gy | 5 × 2 Gy | 1 × 10 Gy | 1 × 20 Gy |
|---|---|---|---|---|---|
| | | cell counts (mean values) | | | |
| CX+ | 100 | 100.0 | 97.8 | 96.6 | 95.0 |
| CX− | 100 | 96.6 | 96.0 | 98.6 | 87.5* |
| Colo+ | 100 | — | — | 97.0 | 88.9 |
| Colo− | 100 | — | — | 90.8 | 80.5* |
| HeLa Bag-4 | 100 | — | — | 97.7 | 96.7 |
| HeLa neo | 100 | — | — | 98.0 | 91.4 |

On day 2 after cell passage, exponentially growing, adherent carcinoma cells were irradiated with different doses. Following a 24 h recovery period at 37° C. cell viability was determined by trypan blue exclusion assays and by Annexin-V staining. Data represent mean values of viable cell counts derived from three independent experiments; — means not tested, *indicates values significant different from control.

Cell viability of HeLa cervix carcinoma cells transfected either with neo vector or mouse Bag-4 was only marginally reduced following irradiation with 1×20 Gy (Table 2).

Figure 1:
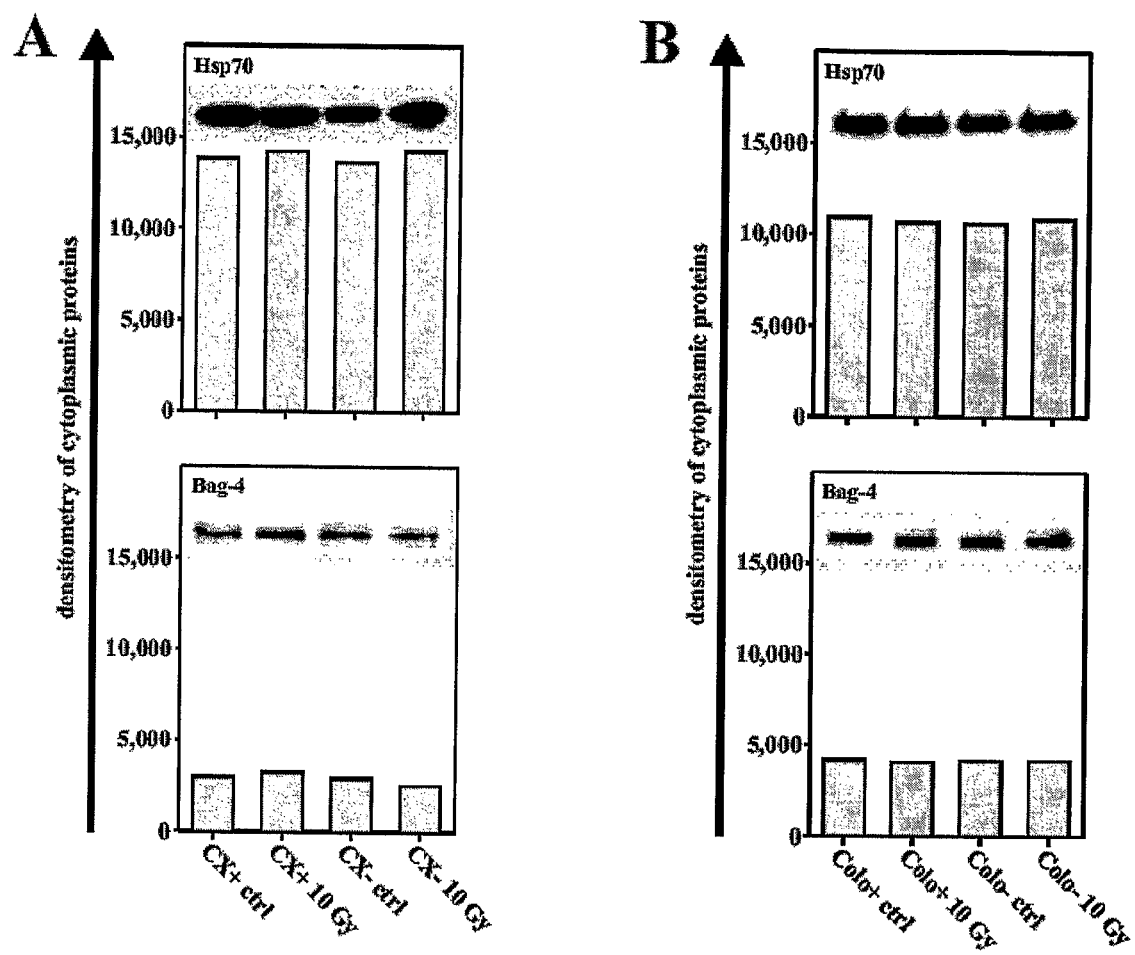
FIG. 1: Cytoplasmic Hsp70 and Bag-4 levels remained unaltered in colon (CX+/CX−) and pancreas (Colo+/Colo−) carcinoma sublines after γ-irradiation. Adherent growing CX+/CX− (A) and Colo+/Colo− (B) carcinoma cells were maintained either untreated (ctrl) or were irradiated (10 Gy). After a recovery period of 24 h, cell lysates were prepared, equal protein amounts (10 μg) were run on a 10% SDS-PAGE, and transferred to nitrocellulose membranes. Western blots were stained with Hsp70-, and Bag-4-specific antibodies (Table 1). Protein bands were analysed by densitometry. Histograms and Western blots show one representative experiment of at least 3 identical.

With respect to these findings, all further experiments were performed with the sublethal γ-irradiation dose of 1×10 Gy, followed by a recovery period of 24 h at 37° C. Although the carcinoma sublines CX+/CX− and Colo+/Colo− differed significantly with respect to their capacity to express Hsp70 on the cell surface, the cytoplasmic Hsp70 levels in each tumor type were identical even after sublethal γ-irradiation (FIG. 1 A and FIG. 1B, upper part). It is well known that Bag-4 binds to the ATPase domain of Hsp70. Therefore, in addition to Hsp70, the cytoplasmic amount of Bag-4, in untreated and γ-irradiated colon (CX+/CX−) and pancreas (Colo+/Colo−) carcinoma sublines was determined. Pancreas carcinoma cells are described to have elevated Bag-4 expression levels (Ozawa et al., Biochem. Biophys. Res. Commun. 271 (2000), 409-413), conferring resistance to TNF-induced cell death. The present data are in line with these findings; the cytoplasmic amount of Bag-4 in Colo+/Colo− pancreas carcinoma sublines (FIG. 1B, lower part), as determined by densitometry, was about twice as much as compared to that of CX+/CX− colon carcinoma sublines (FIG. 1A, lower part), if equal protein amounts were run on a SDS-PAGE. Following sublethal γ-irradiation (1×10 Gy) the cytoplasmic amount of Bag-4, as determined using different anti-bodies recognizing epitopes in the C- and N-terminus of Bag-4 (Table 1), was also not elevated in any of the tumor sublines (FIG. 1A and FIG. 1B, lower part). Identical results were observed with respect to Bag-1.

Figure 2:
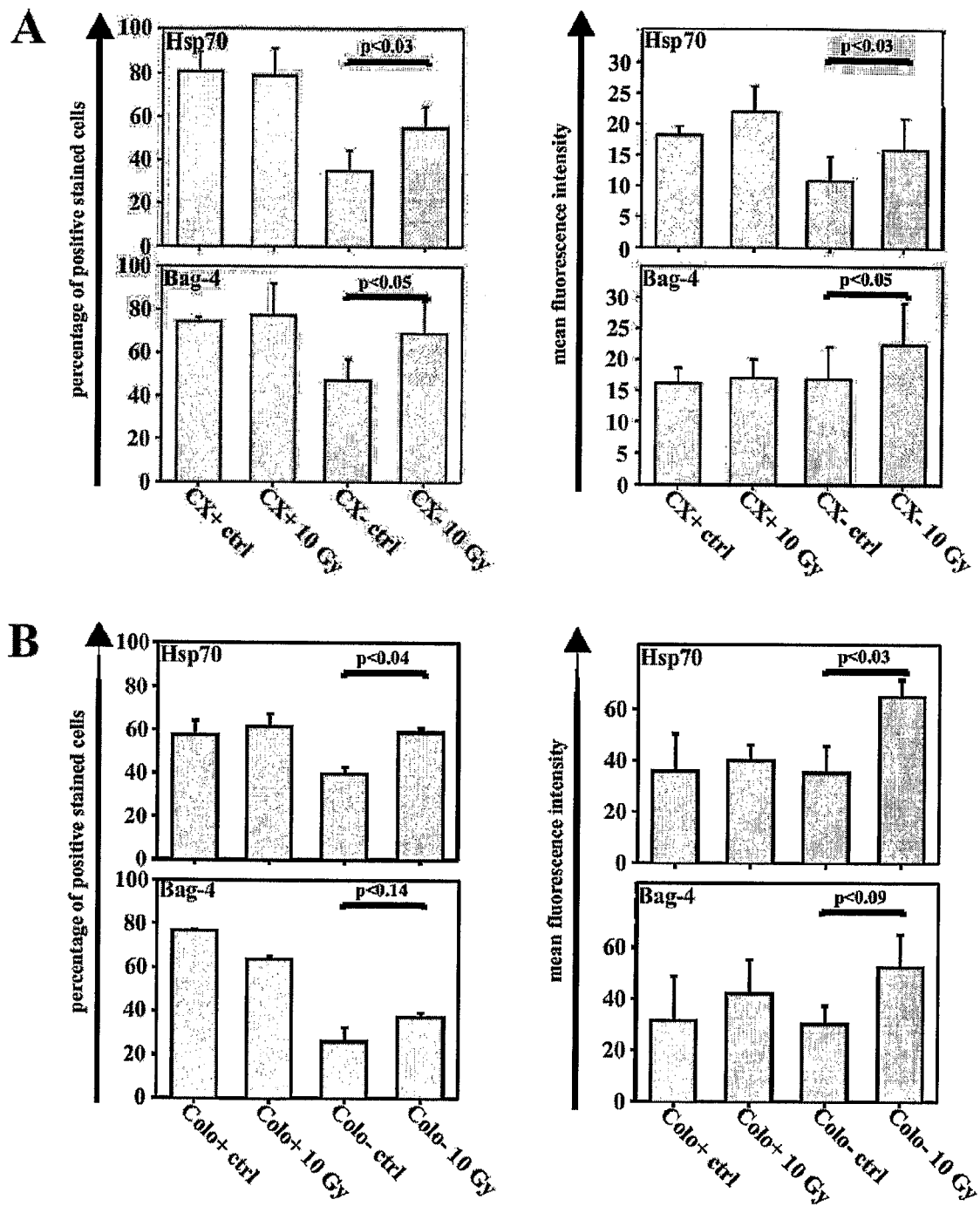
FIG. 2: Cell surface expression of Hsp70 and Bag-4 was upregulated on Hsp70-low expressing colon (CX−) and pancreas (Colo−) carcinoma sublines after γ-irradiation. The percentage of positive cells (left panel) and the mean fluorescence intensity (right panel) of Hsp70 and Bag-4 single stainings were determined by flow cytometry on untreated (ctrl) and γ-irradiated (10 Gy) colon (A: CX+/CX−) and pancreas (B: Colo+/Colo−) carcinoma cells, using Bag-4-specific antibodies recognizing the C-terminal localized BAG domain (Table 1). Histograms represent mean values of 5 independent experiments±SE; differences are indicated as p values.

Although, cytoplasmically no obvious changes were observed after sublethal γ-irradiation, modulations in the cell surface expression pattern of Hsp70 were investigated. As indicated in FIG. 2A (upper graph) the percentage of Hsp70-positive cells remained unaltered high in CX+ carcinoma cells after γ-irradiation (82% versus 81%). However, a significant increase in Hsp70-positivity was detected in CX− carcinoma cells (p<0.03); the percentage of Hsp70-positive cells raised from 34% to 59%. Interestingly, Hsp70 membrane-positive CX+ cells were also found to be strongly positive for Bag-4 (78%), as determined by using two different antibodies (Table 1) recognizing the C-terminal localized BAG domain (FIG. 2A, lower graph). A Bag-4 antibody, recognizing an epitope within the N-terminus, was unable to detect membrane-bound Bag-4. Only 42% of the Hsp70-low expressing CX− cells exhibited a Bag-4 positive phenotype (FIG. 2A, lower graph). Similarly, a significant elevation in Bag-4 expressing cells (42% to 73%) was predominantly found in CX− cells, but not in CX+ cells (78% to 79%). With respect to the mean fluorescence intensity (mfi), determining the protein density per cell, a significant increase in Hsp70 (p<0.03) and Bag-4 (p<0.05) proteins was again detected in CX− cells (FIG. 2A, left panel). No cell surface expression was determined using antibodies directed against Bag-1 or Bag-3 with epitopes situated in the C- or N-terminus. In summary, it could be concluded that sublethal γ-irradiation upregulates Hsp70 and Bag-4 predominantly in carcinoma sublines with initial low expression pattern.

Figure 3:
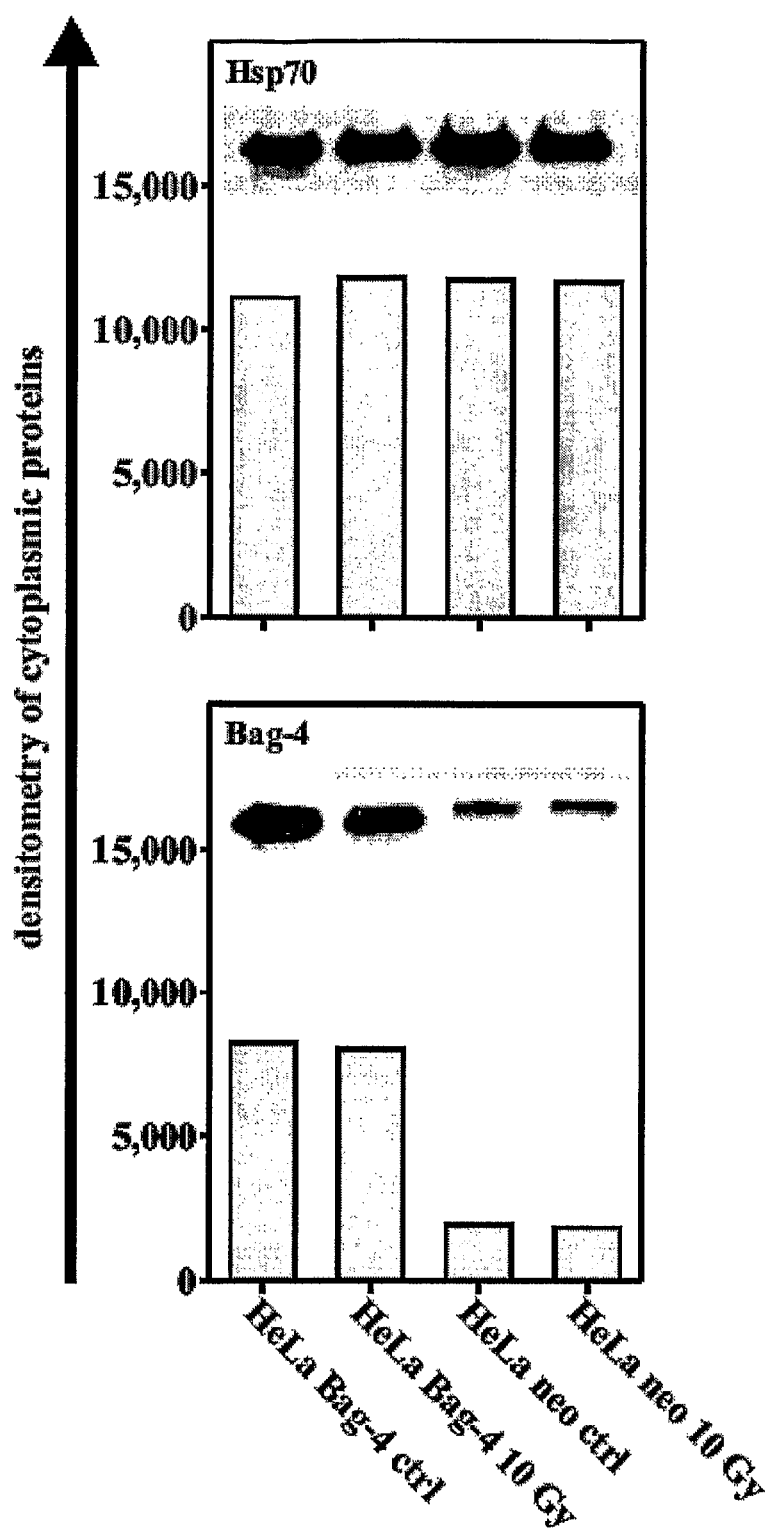
FIG. 3: Cytoplasmic Hsp70 and Bag-4 levels in Bag-4 overexpressing or neo transfected HeLa cervix carcinoma cells remained unaltered after γ-irradiation. HeLa cervix carcinoma transfected with mouse Bag-4 revealed 4-fold increased cytoplasmic Bag-4 levels as compared to neo transfected or untransfected cells. HeLa Bag-4- and neo-transfected carcinoma cells were maintained either untreated (ctrl) or were irradiated (10 Gy). After a recovery period of 24 h, cell lysates were prepared and equal protein amounts (10 μg) were run on a 10% SDS-PAGE, and transferred to nitrocellulose membranes. Western blots were stained with Hsp70-, and Bag-4-specific antibodies (Table 1). Protein bands were analysed by densitometry. Histograms and Western blots show one representative experiment of 4 identical.

These data could be confirmed within the pancreas carcinoma cell system Colo+/Colo−, that was established according to the identical protocol used for the generation of CX+/CX− sublines (Multhoff et al., J. Immunol. 158 (1997), 4341-4350). After cell sorting, using the Hsp70-specific monoclonal antibody, about 60% of the Colo+ cells exhibited an Hsp70 membrane-positive phenotype, but only 37% of the Colo−cells were found to be Hsp70 membrane-positive (FIG. 2B, upper graph). With respect to Bag-4, 78% of the Colo+ cells and 29% of the Colo−cells were membrane-positive (FIG. 2B, lower graph). This phenotype remained stable in both sublines in succeeding cell passages. As already shown for CX+/CX−, and in contrast to the differences detected in the cell surface expression pattern, the intracellular Hsp70/Bag-4 content was identical in Colo+/Colo− cells (FIG. 1B). After sublethal γ-irradiation, only Colo−, but not Colo+ carcinoma cells, exhibited a significant increase (p<0.04) in the percentage of Hsp70 (37% to 58%) and Bag-4 (29% to 39%) positive cells (FIG. 2B). Similar to CX− colon carcinoma cells, the protein density of Hsp70 (p<0.03) and Bag-4 (p<0.04) on a single cell level, was elevated in Colo− cells (FIG. 2B). Regarding these results derived from two independent carcinoma cell systems it was speculated about a co-regulated Hsp70/Bag-4 plasma membrane expression that appears to be independent from the cytoplasmic protein content. To answer the question whether cytosolic Bag-4 might influence Hsp70 expression, mouse Bag-4 was overexpressed in HeLa cervix carcinoma cells. The cytoplasmic amount of Hsp70 and Bag-4 in untreated and irradiated HeLa cells, transfected either with mouse Bag-4 or vector (neo) only, are illustrated in FIG. 3. Bag-4-overexpressing cells exhibited 4-fold higher cytoplasmic Bag-4 levels, as compared to neo-transfected (FIG. 3, lower graph) or untransfected HeLa cells. However, Bag-4 overexpression did not affect cytoplasmic Hsp70 levels (FIG. 3, upper graph). Also, after sublethal γ-irradiation, the cytoplasmic Hsp70 and Bag-4 levels remained indistinguishable from untreated cells (FIG. 3).

Figure 4:
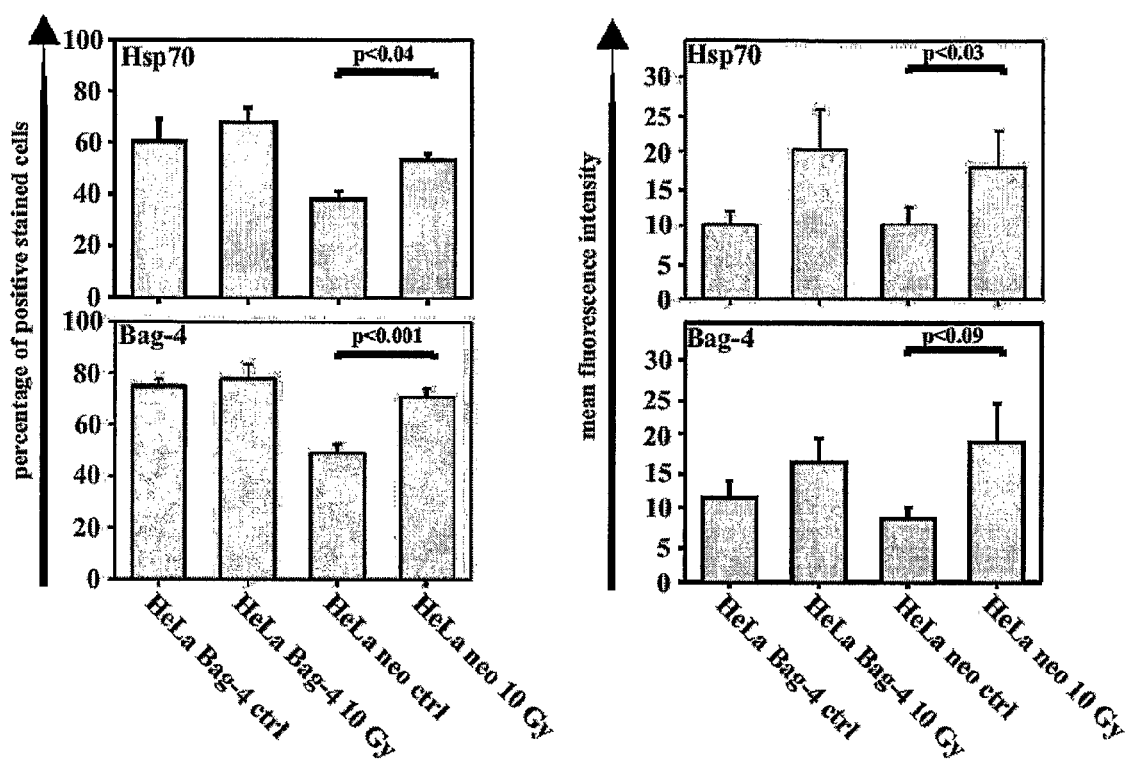
FIG. 4: Cell surface expression of Hsp70 and Bag-4 was upregulated on neo transfected HeLa cells after γ-irradiation. The percentage of positive cells (left panel) and the mean fluorescence intensity (right panel) of Hsp70 and Bag-4 single stainings were determined by flow cytometry on untreated (ctrl) and irradiated (10 Gy) HeLa Bag-4/HeLa neo transfected carcinoma cells, using Bag-4-specific antibodies recognizing the C-terminal localized BAG domain (Table 1).

In contrast to the cytoplasm, striking differences were detected with respect to membrane-bound Hsp70 and Bag-4. As shown in FIG. 4 (left panel), the number of Hsp70-positive cells in Bag-4-transfected HeLa cells was 60%, whereas that in neo-transfected cells was only 38%. Differences in Bag-4 membrane expression were as follows: Bag-4 transfected, 78%; neo-transfected, 49%. Following γ-irradiation a significant increase in the percentage of Hsp70 ($p<0.04$) and Bag-4 ($p<0.001$) positivity was only observed in HeLa neo cells (Hsp70: 38% to 58%; Bag-4: 49% to 76%). As already shown for CX− and Colo−cells, concomitant with the percentage of positively stained cells, also the mfi of Hsp70 ($p<0.03$) and Bag-4 ($p<0.09$) were found to be elevated (FIG. 4, right panel). Taken together, γ-irradiated HeLa neo cells reacted like CX− and Colo−cells, with a significant increase in number and density of Hsp70/Bag-4 on the cell surface, whereas Bag-4-transfected cells were comparable to CX+ and Colo+ cells. It is worth mentioning that untransfected HeLa cells behaved identical to neo-transfected cells.

Example 2

Hsp70 and Bag-4 are Co-Localized on the Cell Surface of Carcinoma Cells

To demonstrate co-localization of Hsp70 and Bag-4 on the cell surface, multiparameter flow cytometry was performed using Hsp70-FITC and Bag-4-PE conjugated antibodies. In FIG. 5A-C, horizontal and vertical lines mark the results derived from staining with isotype-matched control antibodies. Under physiological conditions, a dominant Hsp70/Bag-4 double-positive cell population, found in the upper right corner, was only detectable in CX+, Colo+ and HeLa Bag-4-transfected cells. Following sublethal γ-irradiation, this double-positive cell population did not increase significantly in CX+ (A: 71% to 77%), Colo+ (B: 65% to 75%) and HeLa Bag-4 transfected (C: 73% to 74%) carcinoma cells. In contrast, the number of Hsp70/Bag-4 double-positive stained cells in initially low expressing CX− (A: 35% to 73%), Colo− (B: 34% to 52%) and HeLa neo-transfected (C: 49% to 73%) cells was drastically enhanced, as illustrated by a shift of the cell population from the lower left corner to the upper right corner. These data, supporting the results obtained by single antibody staining (FIG. 2 and FIG. 4), led us to the hypothesis that Hsp70/Bag-4 might be co-localized on the cell surface of tumor cells. To further prove this hypothesis, immunocytochemistry was performed with Hsp70/Bag-4 double-positive carcinoma cells (CX+), using a two-color staining technique. FIG. 6A represents Bag-4-PE single staining in red, and FIG. 6B Hsp70-FITC single staining in green. A yellow color in the overlay of both immunostainings revealed that most Hsp70 and Bag-4 molecules on the plasma membrane are co-localized (FIG. 6C). Light microscopical analysis, as depicted in FIG. 6D, shows a regular cell morphology of the tumor cells. In FIGS. 6E-H the corresponding isotype-matched, negative controls are illustrated for each staining. FIG. 6I represents an Hsp70/Bag-4 staining at a higher magnification (40×); again co-localization is marked by yellow spots caused by an overlay of the green FITC- and red PE-staining (e.g. arrows). A light microscopical view of this cell is shown as FIG. 6J. Identical results were obtained using Colo+, and HeLa Bag-4-transfected cells.

Example 3

Hsp70/Bag-4 Cell Surface Expression Confers Protection Against γ-Irradiation-Induced Effects To study functional consequences of sublethal γ-irradiation in tumor sublines with differential Hsp70/Bag-4 membrane expression pattern, cells were seeded in 96 well plates and incubated with $^3$H-thymidine. After an incubation period of 48 h photographs were taken from representative parts of each cell culture. Initially, growth of Hsp70/Bag-4-high expressing carcinoma cells (CX+, Colo+, HeLa Bag-4) and their -low expressing counterparts (CX−, Colo−, Hela neo) was comparable, as depicted by light microscopical analysis and by $^3$H-thymidine uptake (FIG. 7A-C). As expected, following irradiation (1×10 Gy) the proliferative capacity was reduced in all cell types. However, a comparison of irradiated CX+/CX−, Colo+/Colo−, and HeLa Bag-4/HeLa neo cells revealed that Hsp70/Bag-4-high expressing carcinoma cells were significantly more resistant to irradiation-induced growth inhibition as compared to their -low expressing counterparts. It is known that irradiation-induced effects on cell proliferation is due to a G2/M cell cycle arrest. Therefore, in addition to the $^3$H thymidine uptake assay, cell cycle analysis were performed before and after identical treatment conditions. The typical irradiation-induced G2/M arrest was more pronounced in Hsp70/Bag-4-low expressing CX− (G2/M: 73% versus 58%), Colo− (G2/M: 55% versus 43%) and HeLa neo cells (G2/M: 63% versus 32%), as compared to their Hsp70/Bag-4-high expressing partner cell lines.

Example 4

Irradiation-Induced Hsp70/Bag-4 Membrane Expression is Associated with an Increased Sensitivity Towards Activated NK Cells Previously, the inventors demonstrated that membrane-bound Hsp70 provides a target structure for Hsp70 peptide-activated NK cells (Multhoff et al., Int. J. Cancer 61 (1995), 272-279). Following physical (heat) or chemical (ET-18-OCH3, paclitaxel, vincristinsulfate) stress stimuli the amount of membrane-bound Hsp70 could be increased on the cell surface of tumor cells (Botzler et al., Exp. Hematol. 27 (1999), 470-478; Gehrmann et al., J. Biol. Chem. 383 (2002), 1715-1725; Multhoff et al., Exp. Hematol. 27 (1999), 1627-1636). Concomitantly, an elevated sensitivity to lysis mediated by Hsp70 peptide-activated NK cells was observed. Here, Hsp70 peptide-activated, CD94-positive enriched NK were used as effector cells (Jaattela et al., EMBO J. 17 (1998), 6124-6134). As summarized in Table 3, untreated carcinoma sublines with low Hsp70/Bag-4 membrane expression (CX−, Colo−, HeLa neo) were not lysed as well as their high expressing counterparts (CX+, Colo+, HeLa Bag-4) unless irradiation.

TABLE 3

Comparison of the lytic activity of Hsp70 peptide activated, CD94-enriched (purity: >80%) NK cells against CX+ and CX− tumor cells, either untreated or following sublethal irradiation (1 × 10 Gy, followed by a 24 h recovery period).

| target cells | E:T ratio 20:1 | 10:1 | 5:1 specific lysis (%) ± SE | 2:1 | 1:1 |
|---|---|---|---|---|---|
| CX+ | 73 ± 5.1 | 66 ± 2.5 | 60 ± 0 | 37 ± 1.5 | 31 ± 1.0 |
| CX+ (10 Gy) | 83 ± 2.0 | 80 ± 1.3 | 70 ± 6.0 | 42 ± 2.1 | 37 ± 2.4 |
| CX+ (10 Gy) + HSp70 antibody | 57 ± 5.0 | 32 ± 3.2 | 20 ± 1.5 | 15 ± 3.1 | 9 ± 1.1 |
| CX− | 45 ± 1.2 | 36 ± 3.3 | 21 ± 2.3 | 15 ± 4.0 | 8 ± 1.0 |
| CX− (10 Gy) | 79 ± 3.2 | 68 ± 4.1 | 49 ± 1.2 | 32 ± 2.2 | 10 ± 2.1 |
| CX− (10 Gy) + Hsp70 antibody | 45 ± 3.1 | 30 ± 3.1 | 22 ± 0.0 | 13 ± 2.1 | 5 ± 1.3 |
| Colo+ | 42 ± 2.5 | 31 ± 3.2 | 24 ± 3.5 | 15.5 ± 1.7 | 7.5 ± 3.1 |
| Colo+ (10 Gy) | nt | 33 ± 2.0 | 23 ± 0 | 16 ± 2.0 | 9 ± 2.5 |
| Colo+ (10 Gy) + Hsp70 antibody | 17 ± 3.4 | 16 ± 1.0 | 12 ± 3.0 | 8 ± 1.0 | 5 ± 2.0 |
| Colo− | 29 ± 4.4 | 23 ± 2.5 | 10.0 ± 5.4 | 5 ± 1.9 | 2 ± 0.8 |
| Colo− (10 Gy) | nt | 30 ± 4.0 | 28 ± 2.0 | 18 ± 1.0 | 10 ± 3.0 |
| Colo− (10 Gy) + Hsp70 antibody | 18 ± 3.0 | 19 ± 2.6 | 15 ± 2.1 | 9 ± 2.5 | 1 ± 0 |
| HeLa Bag-4 | 89 ± 1.0 | 77 ± 2.5 | 64 ± 2.5 | 38 ± 3.5 | 22 ± 2.0 |
| HeLa Bag-4 (10 Gy) | 99 ± 1.0 | 98 ± 1.6 | 95 ± 4.0 | 54 ± 5.8 | 34 ± 3.0 |
| HeLa Bag-4 (10 Gy) + Hsp70 antibody | 58 ± 3.0 | 45 ± 4.5 | 40 ± 2.0 | 30 ± 1.0 | 20 ± 2.5 |
| HeLa neo | 60 ± 1.0 | 53 ± 3.6 | 39 ± 2.0 | 15 ± 4.0 | 8 ± 3.0 |
| HeLa neo (10 Gy) | 99 ± 5.0 | 89 ± 7.0 | 72 ± 1.2 | 38 ± 2.0 | 20 ± 0 |
| HeLa neo (10 Gy) + Hsp70 antibody | 63 ± 3.0 | 50 ± 5.0 | 41 ± 4.0 | 19 ± 0 | 10 ± 2.5 |

The cytolytic activity was determined at effector to target cell ratios ranging between 40:1 and 2:1. For blocking experiments, Hsp70-specific monoclonal antibodies (cmHsp70.1, and LR-1; 10 µg for 1 × $10^6$ tumor cells) were co-incubated for 15 min with the tumor target cells directly after labeling with $^{51}$Cr. Percentage spontaneous release of each target cell was below 25%. The data represent the mean of three independent experiments ± SE.

After sublethal γ-irradiation, lysis of Hsp70/Bag-4-positive carcinoma cells remained unaltered high. In contrast, lysis of irradiated Hsp70/Bag-4 low-expressing carcinoma cells was increased significantly in a dose dependent manner (Table 3). Irradiation-induced increased Hsp70/Bag-4 membrane expression (FIG. 2 and FIG. 4), confering resistance to γ-irradiation, corresponded to an enhanced sensitivity towards NK cell-mediated cytotoxicity. Antibody blocking assays revealed an inhibition of lysis of irradiated carcinoma cells by the Hsp70-specific antibody (clone cmHsp70.1). This antibody is known to detect the Hsp70 epitope exposed to the extracellular milieu of tumor cells. Presumably, this epitope is also involved in the recognition of irradiated tumor cells. In contrast, blocking studies using two different Bag-4 specific antibodies (Table 1) directed against the carboxy-terminal localized BAG domain, revealed no inhibition in lysis.

Example 5

Production of Bispecific F(ab')$_2$ Antibody Fragments

In principle, intact polyclonal or monoclonal anti-Hsp70 and anti-Bag antibodies, respectively, see supra, can be used to prepare bispecific antibody fragments; see, e.g., Brennan et al., Science 229 (1985), 81-83. For example, intact anti-Hsp70 and anti-Bag antibodies used in examples 1-4 are fragmented by peptic (three hours at 37° C. in acetate buffer of pH 4.0, Pepsin from Sigma) digestion to F(ab')$_2$ fragments to cleave off the Fc portion of the antibody. The reaction is terminated by increasing the pH value to 8 with Tris buffer and the resulting F(ab')2 fragments are purified by column chromatography (e.g. Superdex 200 column). Then, the disulfide bonds of the hinge region of the purified F(ab')$_2$ molecule are digested by reduction in the presence of arsenite and the F(ab')-SH fragments thus obtained are again purified by column chromatography, so as to then modify the reduced SH groups with the Ellman's reagent (DTNB) to F(ab')-TNB (incubation for 20 hours at room temperature with an equal volume of a mixture of 5,5'-dithiobis-2-nitrobenzoic acid (DTNB; Sigma) and thionitrobenzoate (TNB) with a molar ratio of the DTNB-TNB mixture of 20:30 and adjustment by incubating for a few minutes a 40 mM DTNB solution with a 10 mM DTT solution). After further purification by column chromatography one of the two antibody fragments is reduced to F(ab')-SH (0.1 mM DTT (Sigma) for one hour at 25° C.), purified by column chromatography and hybridized to the other F(ab')-TNB fragment (1 hr at 25° C.) to give a bispecific F(ab')$_2$ fragment. Finally, the bispecific antibody fragments thus obtained are purified by gel chromatography.

The bispecific molecule may be further modified, for example labeled with a fluorescent dye and tested, inter alia, for the binding to human tumor material, the activity in lymphocyte proliferation and cytotoxicity tests and the stability under in vivo conditions, for example incubation in human serum at 37° C.

Summary

As described in the examples, the effects of sublethal γ-irradiation were analysed in three independent carcinoma cell systems, with initially different Hsp70 membrane expression pattern. Apart from Hsp70, members of the Bag family are involved in regulating programmed cell death. In humans, six Bag family members could be identified, all sharing a conserved Bag-domain and a quite variable N-terminus. Four of the six members bind to the ATPase domain of Hsp70 and Hsc70 (Takayama et al., J. Biol. Chem. 274 (1999), 781-786). Furthermore, Bag proteins interact with different cell surface receptors. The Bag-1M isoform in concert with Hsp70/Hsc70 interact with retinoic acid receptors, glucocorticoid, estrogen, and thyroid hormone receptors (Takayama and Reed, Nat. Cell Biol. 3 (2001), 237-241; Takayama et al., Cell 80 (1995), 279-284; Takayama et al., EMBO J. 16 (1997), 4887-4896; Liu et al., J. Biol. Chem. 273 (1998), 16985-16992; Kanelakis et al., J. Biol. Chem. 274 (1999), 34134-34140; Song et al., Nat. Cell Biol. 3 (2001), 276-282), thus mediating stress-signaling pathways that regulate Raf-1/ERK and cell growth (Doong et al., Oncogene 19 (2000), 4385-4395). Bag-3 forms an EGF-regulated ternary complex with phospholipase C-γ and Hsp70/Hsc70, thus presenting a link between transmembrane signaling and the Hsp70 system, shown in human melanoma cells (Liao et al., FEBS Lett. 503 (2001), 151-157; Thress et al., EMBO J. 17 (1998), 6135-6143). Bag-6, first described in *Xenopus*, interacts with apoptosis-inducing factor reaper in *Drosophila* cells (Jiang et al., Science 283 (1999), 543-546). These investigations point at a relationship between plasma membrane-localized receptors, Hsp70 and Bag proteins. It is conceivable that following stress Hsp70 and under physiological conditions Hsc70 might serve as regulators coupling function of Bag proteins to plasma membrane localized receptors. The plasma membrane is a complex, multifunctional structure, far beyond from a simple lipid bilayer, separating the intracellular from the extracellular milieu. The intercellular cross-talk depends on cytosolic proteins and receptors, in and on the plasma membrane. Since Hsp70 is a major player in transport processes across membranes, it is possible that in concert with Bag proteins, Hsp70 might fulfill regulatory functions in apoptotic cell death not only in the cytosol but also on the plasma membrane.

In the present study the interaction of Hsp70 with Bag-4, also termed silencer of death domain (SODD) was investigated, since other members of the Bag family were not detected on the cell surface. Although the tumor sublines differed significantly with respect to their capacity to present Hsp70 on the cell surface, the intracellular Hsp70 levels were identical. Even after sublethal γ-irradiation the cytoplasmic Hsp70 content remained unaltered. Comparable results were obtained for cytosolic Bag-4. In contrast to the cytosol, following irradiation the amount of membrane-bound Hsp70 was significantly up-regulated in tumor sublines with initial low Hsp70 cell surface expression. Interestingly, the Hsp70 membrane-positive phenotype was associated with Bag-4 cell surface localization. Co-localization of Hsp70 and Bag-4 was demonstrated by two-color flow cytometry and immunocytochemistry. This indicates that Hsp70/Bag-4 protein complexes not only exist in the cytosol, but also on the plasma membrane. It was found that only antibodies directed against the C-terminal localized domain of Bag-4, interacting with the ATPase domain of Hsp70, but not antibodies against the N-terminus, were able to detect Bag-4 on the cell surface of viable tumor cells with intact plasma membrane. This suggested that the N-terminal domain of Bag-4 might not be accessible from outside of the cell. Furthermore, due to sterorical masking of the ATPase domain of Hsp70 by Bag-4 binding, the present data might provide an explanation for the finding that antibodies directed against the ATPase domain of Hsp70 were unable to recognize cell membrane-bound Hsp70.

It has been reported that Hsp70 associated with Bag-4 binds to the death domain of tumor necrosis factor 1 (TNFR1) or death receptor 3 (DR3) and thus prevents self aggregation to functional trimers initiating caspase-dependent apoptotic cell death (Wei et al., Cancer Immunol. Immunother. 40 (1995), 73-78). Therefore it is believed that membrane-bound Hsp70/Bag-4 might also be linked to the cytoplasmic domain of TNFR1. However, neither CX+/CX− nor Colo+/Colo− carcinoma sublines exhibited TNFR1 or DR3 membrane expression. Furthermore, incubation of the carcinoma cells with TNF-α either alone or in combination with cycloheximid, did not induce apoptosis. Regarding these results it was speculated about a TNFR1/DR3 independent cell surface translocation of Hsp70/Bag-4. Besides its function in apoptosis signaling, Hsp70 plays a pivotal role in cell cycle control. Treatment of tumor cells with Hsp70 anti-sense oligomers leads to inhibition of proliferation and initiation of apoptosis in tumor cell lines (Multhoff et al., J. Immunol. 158 (1997), 4341-4350). It had been suggested that overexpression of Hsp70 reduces radiation-induced cell cycle arrest in the G2/M phase. The present experiments provide evidence that not cytoplasmic, but cell membrane-bound Hsp70/Bag-4 protein complexes confer protection against irradiation-induced effects. In unstressed cells the proliferative capacity was comparable in Hsp70-high and -low expressing tumor sublines. In contrast, following sublethal irradiation, Hsp70/Bag-4 membrane localization appeared to be more resistant to growth arrest.

The Hsp70 epitope, exposed to the extracellular milieu of the plasma membrane (Jaattela et al., EMBO J. 17 (1998), 6124-6134) could be defined as immunogenic for NK cells (Multhoff et al., J. Immunol. 158 (1997), 4341-4350). The capacity of Hsp70 and peptides derived thereof, eliciting a cellular immune response, is in line with observations of others. Several receptors on the surface of immunoregulatory cells, including CD40 on B cells (Becker et al., J. Cell Biol. 158 (2002), 1277-1285), CD14 and toll like receptors on monocytes and dendritic cells (Asea et al., Nat. Med. 6 (2000), 435-442), CD91 on macrophages (Binder et al., Nat. Immunol. 1 (2000), 151-155), and CD94 on NK cells (Gross et al., J. Biol. Chem. 384 (2003), 267-279) have been identified, enabling interaction and uptake of Hsp70. Here it is shown that tumor sublines expressing high amounts of Hsp70/Bag-4 on their cell surface are better protected against γ-irradiation-induced effects, as compared to their low expressing counterparts, and thus might confer radioresistance. However, on the other hand these tumor cells provide ideal targets for the cytolytic attack mediated by Hsp70 peptide-activated NK cells. Contact of NK cell with the extracellular localized Hsp70 epitope has been found to stimulate synthesis and secretion of granzyme B, an apoptosis-inducing enzyme (Gross et al., J. Biol. Chem. (2003), Jul. 21). Membrane-bound Hsp70 facilitates uptake of granzyme B into tumor cells, and thus induces apoptotic cell death. Antibody blocking studies confirmed that the Hsp70 epitope presented on tumor cells indeed acts as a recognition site for Hsp70 peptide-activated NK cells. In the present experiments it is demonstrated that Hsp70 is co-localized on the plasma membrane with Bag-4. Therefore, it is expected that both molecules, Hsp70 and Bag-4, are involved in the recognition by NK cells. However, although different antibodies were able to detect membrane-bound Bag-4 on tumor cells, none of them exhibited blocking activity. Since only a minority of antibodies are able to inhibit effector cell mediated cell kill, a role for Bag-4 as a recognition site for NK cells cannot be completely ruled out.

The experiments according to the present invention have shown that membrane-bound Hsp70/Bag-4 prevents tumor cells from irradiation-induced effects. Therefore, Hsp70/Bag-4 membrane expression is expected to be useful as a prognostic marker and target for therapy-resistant tumor cell clones. In addition, evidence is provided for Hsp70/Bag-4 as a target recognition structure for NK cell-mediated cytotoxicity. Therefore, it is reasonable to expect that γ-irradiated tumor patients profit from Hsp70-activated NK cells that might support the eradication of tumor clones with increased Hsp70/Bag-4 membrane expression.

The invention claimed is:

1. A bispecific immunoglobulin molecule that comprises a first binding domain comprising $V_L$ and $V_H$ domains of monoclonal antibody cmHsp70.1 as produced by hybridoma cmHsp70.1, deposited with the DSMZ-Deutsche Sammlung von Mikroorganismen und Zellkulturen GmbH, Mascheroder Weg 1 b, D-38124 Braunschweig, Germany on Nov. 14, 2003, and assigned Accession Number DSM ACC2629 or $V_L$ and $V_H$ domains of monoclonal antibody cmHsp70.2 as produced by the hybridoma cmHsp70.2, deposited with the DSMZ-Deutsche Sammlung von Mikroorganismen und Zellkulturen GmbH on Nov. 14, 2003, and assigned Accession Number DSM ACC2630 which binds cell surface membrane-bound heat shock protein 70 (Hsp70) and a second binding domain comprising $V_L$ and $V_H$ domains which binds a member of the anti-apoptotic Bcl-2-associated athanogene (Bag) family, wherein the bispecific molecule is capable of specifically binding its target antigen on viable tumor cells.

2. The bispecific molecule of claim 1, wherein said member of the Bag family is Bag-4.

3. The bispecific molecule of claim 1, wherein said first binding domain binds to the C-terminal domain of the Hsp70 and said second binding domain binds to the C-terminal domain of Bag protein.

4. The bispecific molecule of claim 1, which is a dimeric molecule.

5. The bispecific molecule of claim 1, which has at least one further functional domain.

6. The bispecific molecule of claim 5, wherein said further functional domain is a cytotoxic agent or a label.

7. The bispecific molecule of claim 3, wherein said first binding domain binds human Hsp70 at amino acid residues 454-461 or 450-463.

8. The bispecific molecule of claim 3, wherein said second binding domain binds human Bag-4 at amino acid residues 443-457.

* * * * *